US012678313B2

(12) United States Patent
Hanft

(10) Patent No.: US 12,678,313 B2
(45) Date of Patent: Jul. 14, 2026

(54) AMBULATORY PROTECTIVE DEVICE

(71) Applicant: Foot Defender LLC, Miami, FL (US)

(72) Inventor: Jason R Hanft, Miami, FL (US)

(73) Assignee: Foot Defender LLC, Miami, FL (US)

( * ) Notice: Subject to any disclaimer, the term of this patent is extended or adjusted under 35 U.S.C. 154(b) by 679 days.

(21) Appl. No.: 18/091,637

(22) Filed: Dec. 30, 2022

(65) Prior Publication Data

US 2023/0134968 A1 May 4, 2023

Related U.S. Application Data

(63) Continuation-in-part of application No. 17/575,081, filed on Jan. 13, 2022, now abandoned, which is a continuation of application No. 16/136,722, filed on Sep. 20, 2018, now Pat. No. 11,253,383.

(51) Int. Cl.
*A61F 5/01* (2006.01)
*A61H 3/00* (2006.01)

(52) U.S. Cl.
CPC .......... *A61F 5/0111* (2013.01); *A61F 5/0195* (2013.01); *A61H 3/00* (2013.01)

(58) Field of Classification Search
CPC ........ A61F 5/0195; A61F 5/01; A61F 5/0111; A61F 5/0127; A61F 5/0585; A61F 5/0113; A61F 13/043; A61F 13/066; A61F 13/045; A61F 2005/0167; A43B 3/242; A43B 5/1691; A43B 7/20; A43B 7/14; A61H 3/00
USPC ................. 602/5, 12, 23, 27, 28, 62, 65, 67; 128/882; 36/83, 85, 88–89, 101, 110
See application file for complete search history.

(56) References Cited

U.S. PATENT DOCUMENTS

| | | | |
|---|---|---|---|
| 1,907,136 A | 5/1933 | Weitsen | |
| 2,089,384 A | 8/1937 | Levitt | |
| 3,148,678 A | 9/1964 | Roberts | |
| 3,841,005 A | 10/1974 | Cox | |
| 4,803,989 A | 2/1989 | Collins | |
| 5,078,128 A | 1/1992 | Grim et al. | |

(Continued)

FOREIGN PATENT DOCUMENTS

| | | |
|---|---|---|
| CN | 203424395 U | 2/2014 |
| CN | 214072067 U | 8/2021 |

(Continued)

OTHER PUBLICATIONS

International Search Report, date of mailing Jan. 31, 2020.

*Primary Examiner* — Caitlin A Carreiro
(74) *Attorney, Agent, or Firm* — RPG Law Group; Richard P. Gilly

(57) ABSTRACT

An ambulatory protective device is configured to be worn on a person's foot who has a foot condition, such as a diabetic foot condition. The ambulatory protective device includes an insole which has viscoelastic inserts located and otherwise disposed relative to non-viscous polymeric foam strata to create zones or areas on the insole characterized by reduced force or contact pressure when subjected to forces from the foot during ambulation when the ambulatory protective device is worn. Such contact-pressure reducing areas are located in the heel area and the forefoot area of the device. The ambulatory protective device, equipped with such insole, may be in the form of a shoe, boot, brace, cast, or walker, such as a CAM walker.

12 Claims, 19 Drawing Sheets

(56) References Cited

U.S. PATENT DOCUMENTS

| | | | |
|---|---|---|---|
| 5,317,820 | A | 6/1994 | Bell et al. |
| 5,368,551 | A | 11/1994 | Zuckerman |
| 5,369,896 | A | 12/1994 | Frachey et al. |
| 5,400,529 | A | 3/1995 | Bell et al. |
| 5,425,701 | A | 6/1995 | Oster et al. |
| 5,571,078 | A | 11/1996 | Malewica |
| 5,746,011 | A | 5/1998 | Hedstrom |
| 5,787,608 | A | 8/1998 | Greenawalt |
| 6,409,695 | B1 | 6/2002 | Connelly |
| 7,159,342 | B2 | 1/2007 | Grisoni et al. |
| 7,200,955 | B2 | 4/2007 | Foxen |
| 7,303,538 | B2 | 12/2007 | Grim et al. |
| 7,524,295 | B1 | 4/2009 | Peters et al. |
| 7,685,741 | B2 | 3/2010 | Friedman |
| 9,180,038 | B2 | 11/2015 | Ingimundarson et al. |
| 10,638,813 | B2 | 5/2020 | Lovell et al. |
| 10,849,387 | B2 | 12/2020 | Bruce et al. |
| 2004/0118017 | A1 | 6/2004 | Dalton et al. |
| 2005/0172517 | A1* | 8/2005 | Bledsoe ................... A43B 7/28 |
| | | | 36/110 |
| 2007/0293798 | A1 | 12/2007 | Hu |
| 2009/0145003 | A1 | 6/2009 | Kim |
| 2009/0227927 | A1 | 9/2009 | Frazer |
| 2009/0287127 | A1 | 11/2009 | Hu et al. |
| 2009/0287128 | A1 | 11/2009 | Ingimundarson et al. |
| 2012/0017467 | A1* | 1/2012 | Whitney ............. A43B 3/0031 |
| | | | 36/31 |
| 2012/0192452 | A1 | 8/2012 | Lewis et al. |
| 2013/0018294 | A1 | 1/2013 | Jones |
| 2013/0081306 | A1 | 4/2013 | Park et al. |
| 2014/0075777 | A1* | 3/2014 | Bruce ................... A43B 7/148 |
| | | | 36/29 |
| 2014/0276301 | A1 | 9/2014 | Grim |
| 2014/0316316 | A1 | 10/2014 | Andrews et al. |
| 2015/0164179 | A1 | 6/2015 | Walborn et al. |
| 2016/0045354 | A1 | 2/2016 | Lee et al. |
| 2016/0066647 | A1 | 3/2016 | Handorf |
| 2016/0213506 | A1 | 7/2016 | Chen |
| 2016/0324666 | A1 | 11/2016 | Barberio |
| 2016/0345667 | A1 | 12/2016 | Kohatsu et al. |
| 2016/0360825 | A1 | 12/2016 | Pedersen |
| 2017/0165093 | A1 | 6/2017 | Huttenlocker et al. |
| 2021/0000218 | A1 | 1/2021 | Ophir et al. |

FOREIGN PATENT DOCUMENTS

| | | | |
|---|---|---|---|
| EP | 1227774 B1 | 3/2003 | |
| GB | 2221378 A * | 2/1990 | ............. A43B 13/20 |
| KR | 200328467 Y1 | 9/2003 | |
| KR | 20210001973 U | 9/2021 | |
| WO | 2007086806 A1 | 8/2007 | |
| WO | 2016008458 A2 | 1/2016 | |
| WO | 2021156717 A1 | 8/2021 | |

* cited by examiner

DEFENDER VISCOELASTOMER PHYSICAL PROPERTIES (GEL)

| TEST | METHOD | UNITS | RESULT | ASTM METHOD | ASTM UNITS | RESULT |
|---|---|---|---|---|---|---|
| VISCOSITY (RAW) | GB/T 265 | C/PS | 400+/-50 | N/A | N/A | N/A |
| TEST SLAB | CALIPER | MM | 2 | CALIPER | IN | 0.0787402 |
| DUROMETER | SATRA TM205 | SHORE C | 35+/-3 | SATRA TM205 | SHORE C | 35+/- |
| DENSITY | ISO 2781 | G/CM3 | 1.10+/-0.02 | ASTME D 792-13 | LB/FT3 | 80 |
| ELONGATION | ISO 34-1 | % | 300 | ASTM D 412-06A | % | 300 |
| TENSILE STRENGTH | ISO 34-1 | KG/CM2 | 200%+/-2% | ASTM D 412-06A | PSI | 14.06 |
| SPLIT TEAR | ISO 34-1 | KG/CM | 4+/-0.4 | ASTM D 624-00, DIE C | LB/IN | 11.2 |
| COMPRESSION SET | SATRA TM64 | % (MAX) | 10 | ASTM D 395 | % | 10 |
| REBOUND | SATRA TM64 | % (MIN) | 5 | ASTM D 2632-92 | % | 5 |

FIG. 20

DEFENDER ETHYLENE VINYL ACETATE (EVA) PHYSICAL PROPERTIES

| TEST | METHOD | UNITS | RESULT | ASTM METHOD | ASTM UNITS | RESULT |
|---|---|---|---|---|---|---|
| VISCOSITY (RAW) | N/A | PELLET | N/A | N/A | N/A | N/A |
| TEST SLAB | CALIPER | MM | 10MM | CALIPER | IN | 0.393701 |
| DUROMETER | SATRA TM205 | SHORE C | 27+/-3 | SATRA TM205 | SHORE C | 27+/-3 |
| DENSITY | ISO 1183 | G/CM3 | 0.18+/-0.02 | ASTME D 792-13 | LB/FT3 | 11.237 |
| ELONGATION | ISO 16365 | % | 100-150 | ASTM D 412-06A | % | 100-150 |
| TENSILE STRENGTH | ISO 16365 | KG/CM2 | 1.5+/-0.5 | ASTM D 412-06A | PSI | 21.335 |
| SPLIT TEAR | ISO 16365 | KG/CM | 1.5+/-0.5 | ASTM D 624-00, DIE C | LB/IN | 8.39961 |
| COMPRESSION SET | SATRA TM64 | % (MAX) | 30+/-10 | ASTM D 395 | % | 30+/-10 |
| REBOUND | SATRA TM64 | % (MIN) | 46+/-5 | ASTM D 2632-92 | % | 46+/-5 |

FIG. 21

| DEFENDER POLYETHER (POLYURETHANE) PHYSICAL PROPERTIES | | | | | | |
|---|---|---|---|---|---|---|
| TEST | METHOD | UNITS | RESULT | ASTM METHOD | ASTM UNITS | RESULT |
| VISCOSITY (RAW) | GB/T 265 | C/PS | N/A | N/A | N/A | N/A |
| TEST SLAB | CALIPER | MM | 10MM | CALIPER | IN | 0.393701 |
| DUROMETER | SATRA TM205 | SHORE C | 27+/-3 | SATRA TM205 | SHORE C | 27+/-3 |
| DENSITY | ISO 1183 | G/CM3 | 0.34+/-0.02 | ASTME D 792-13 | LB/FT3 | 21.2255 |
| ELONGATION | ISO 13360 | % | 400-450 | ASTM D 412-06A | % | 400-500 |
| TENSILE STRENGTH | ISO 13360 | KG/CM2 | 3.3+/-0.5 | ASTM D 412-06A | PSI | 46.937 |
| SPLIT TEAR | ISO 13360 | KG/CM | 3+/-0.5 | ASTM D 624-00, DIE C | LB/IN | 16.7992 |
| COMPRESSION | SATRA TM64 | % (MAX) | 50+/-10 | ASTM D 395 | % | 50+/-10 |
| REBOUND | SATRA TM64 | % (MIN) | 42+/-5 | ASTM D 2632-92 | % | 42+/-5 |

FIG. 22

Average Contact Over 3 min on Treadmill 1.5mph 4% Grade Healthy Subjects 200lbs male, US Size 12 Shoe

Forefoot Avg Contact Pressure
Heel Avg Contact Pressure
1st Met Head Avg Contact Pressure
2-4 (central) Met Head Avg Contact Pressure

PSI

AMBULATORY PROTECTIVE DEVICE

FIELD

This disclosure relates to lower extremity walkers and, in particular, to walkers and other ambulatory protective devices for use with diabetic foot wounds.

BACKGROUND

Ambulatory protective devices, such as CAM walkers, that is, "Controlled Ankle Movement" walkers, are available in a variety of shapes and sizes. Among their purposes, such leg walkers immobilize the ankle joint, protect portions of the lower extremity, or otherwise treat or address a variety of conditions of the lower extremity.

While certain CAM walkers may include panels or portions to increase or decrease the leg height of such walkers, such designs suffer from various drawbacks and disadvantages. For example, adjustable-height walkers are often complex to manipulate or otherwise not suited to various lower extremity treatment protocols, such as when lower extremities are casted.

Devices which may be associated for use with rigid or semi-rigid casted lower extremities may also suffer from various drawbacks and disadvantages, including their limited application and disadvantageous offloading or other therapeutic characteristics.

Due to the limited adaptability and other drawbacks of CAM walkers of the current art, medical practitioners, hospitals, and other care centers are often required to "double up" on CAM walkers, or otherwise stock and make use of discreet CAM walkers for different treatment phases or lower extremity conditions, thereby causing excess inventory and wasteful inefficiency in the healthcare system in general, and to patients and care providers in particular.

Ambulatory protective devices, such as CAM walkers, generally include footbeds upon which the wearer's foot is placed. The footbeds of many ambulatory protective devices are often little more than a padded topcover and thus often include little to no structure characterized as an insole, such ambulatory protective devices instead relying on excessive padding or other devices to protect the user's foot received on such footbed.

In the case of footbeds formed into or associated with more supportive structures, and thus more characterizable as insoles in the current art, such insoles suffer from various drawbacks and disadvantages. For example, while cushioning insoles, insoles with firmer portions, or insoles with viscoelastic or gel portions might be known in retail or consumer applications, often associated with sports activities for the average wearer, such comfort insoles of the current art, regardless of shape, differing materials, or contours, do not adequately address specific needs of a wearer of an ambulatory protective device, such as a protective shoe, protective boot, CAM walker, other braces, and casts. Such ambulatory protective devices are generally worn when the user's foot has an injury, such as a foot wound or foot ulcer, or is suffering from pain or medical condition, such as neuropathy, such conditions often associated with those with diabetic conditions.

Accordingly, to the extent they have insoles of the current art, ambulatory protective devices, when worn by a diabetic or other user with a foot wound, do not adequately relieve associated medical foot conditions, do not sufficiently protect vulnerable feet which may have, or are susceptible to, the foregoing medical conditions, nor do devices of the current art promote effective healing of foot wounds, ulcers, or other conditions. These shortcomings of insoles and their associated ambulatory protective footwear are especially prevalent, as alluded to above, in devices prescribed or adapted for use in treating and protecting the feet of diabetics. This state of the art has resulted in a statistic that 24% of all diabetic foot wounds lead to limb amputation within 6-18 months of initial evaluation.

In view of the foregoing, despite the availability of polymeric materials with different physical properties, the insoles of ambulatory protective footwear of the current art have not been designed to adequately address the needs for protecting and healing the feet of diabetics during ambulation, and thus lessening the risk of limb amputation.

Accordingly, it would be desirable to address the foregoing drawbacks and disadvantages with an improved ambulatory protective device or CAM walker.

SUMMARY

In one possible implementation, according to the present disclosure, an ambulatory protective device is configured to be worn on a person's foot who has a foot condition, such as a diabetic foot condition. The ambulatory protective device is generally configured to reduce forces on the foot condition so as to reduce pain, promote healing, and accomplish other therapeutic benefits. So, for example, the ambulatory protective device may include an insole which is configured so that, when the ambulatory protective device is worn during ambulation by the person, the average contact pressure in the heel area and the forefoot area on the foot wearing the device is reduced from that otherwise present without the insole of the present disclosure. The insole extends medially, laterally, distally, and proximately, so as to define a footbed within the ambulatory protective device.

In certain implementations, the ambulatory protective device may have a frame which extends from the footbed. Such frame may include a posterior and an anterior portion, as well as distal and proximal ends which are configured to engage corresponding portions of the foot and calf of the person wearing the device. The insole in such implementations may include a top layer, a middle layer located under the top layer, and a bottom layer located under the middle layer. The middle layer has a stratum in which open trays are formed. These open trays, in certain implementations, are located in the forefoot and heel areas, respectively, so as to underly the forefoot and heel of the person when the device is being worn.

The middle layer likewise includes inserts which consist essentially of viscoelastic material or gel, and these inserts are received in the above-mentioned open trays. While the inserts may consist essentially of viscoelastic material, the stratum of the middle layer consists essentially of polymeric foam material. The compression set and rebound values associated with the polymeric foam material are sufficiently higher than the compressions set and rebound values associated with the viscoelastic inserts. As such, the insole, when worn during ambulation, reduces the average contact pressure in the heel area and the forefoot area, up to 30% reduction in certain implementations, as compared to ambulation occurring without the insole of such device.

In further implementations, the compression set value of the polymeric foam material may be at least 200% higher than that of the viscoelastic insert, and the rebound value of the polymeric foam material may be at least 800% higher than the rebound value of the viscoelastic insert.

In further implementations, the above-mentioned open trays are bounded by circumferential walls which define the sides of the open trays, and the trays are further bounded above and below by overlying and underlying planar polymeric foam portions, which thus form the tops and bottoms of the trays. The inserts are configured so that their outer edges are spaced from their circumferential side walls and thereby form circumferential gaps between the inserts and the sidewalls of the stratum. These circumferential gaps have dimensions which are sufficient so that the viscoelastic inserts and the opposing circumferential walls of the stratum remain separated from each other even when the insole is subjected to the predetermined maximum weight normally associated with the person wearing the device. As such, the physical properties associated with the viscoelastic insert, such as reducing contact pressure on the forefoot and heel areas, are not affected by any contact which may otherwise arise between opposing portions of the outer edges of the viscoelastic inserts and the sides of the trays.

In still other implementations, a CAM walker or other ambulatory protective device may include a frame which controls ankle movement of the lower extremity. The frame, when worn, has a distal frame end at or near the foot and a proximal frame end generally above the ankle, each frame end adapted to operatively engage, whether directly or indirectly, portions of the foot and calf, respectively, when the frame is being worn. The CAM walker may include a collar assembly which is selectively fittable to, and manually separable from, the proximal end of the frame. As such, a medical practitioner, to address therapeutic needs, for example, may take actions with the CAM walker of this disclosure to fit the collar assembly to the proximal end of the frame; may forego attachment of the collar to the frame; or, if the collar were previously attached, may separate such collar from the frame, such as in response to other therapeutic needs.

In one variation of the implementations disclosed herein, the CAM walker frame has a foot bed with lateral and medial sides. The frame of the CAM walker, in turn, has corresponding lateral and medial frame elements which partially define a frame circumference and a corresponding frame volume, the circumference and volume being sufficient so that they are capable of receiving not only an ankle and corresponding lower extremity therein, but such ankle and lower extremity therein when wearing the other brace device received in the CAM walker.

In implementations of the present disclosure, the insole may be configured to provide greater protection, force redistribution, force reduction, or other therapeutic benefits to wearers of a variety of ambulatory protective footwear, equipped with an insole having trays with viscoelastic inserts received therein in a spaced manner. Such insole may be formed as a multilayer, force reducing insole, that and its construction may be considered to not only utilize the mechanical properties of different materials, but combine such materials in a fashion such that the mechanical force reduction and therapeutic benefits resulting are greater than the mechanical abilities of each of the materials alone.

Although this disclosure applies to ambulatory protective footwear for adding protection to a user's foot in any suitable application, this disclosure may find particular application to patients with medically diagnosed foot pain, foot wounds, or other foot injuries requiring the use of a protective boot, such as patients with diabetic foot conditions.

In certain implementations, the insole of the instant disclosure may be of four layer construction and is designed to interface with the human foot for use within, or affixed to, shoes, boots, braces, casts, or other types of footwear. The insole described herein in one implementation is part of ambulatory protective footwear, such as a protective boot.

In further implementations, the four layers, or strata, may comprise materials of different resilience, compression, and related characteristics. Significantly, the third such stratum is constructed from foam having open or closed cells of medium density and durometer, and such third stratum is configured to have open chambers or trays formed therein that are located directly under the anatomical areas of the user's heel and forefoot.

In such implementations, the openings of such trays are sized to receive viscoelastic inserts or pods therein, such inserts or pods having a lower durometer preferably than the adjacent portions comprising the third layer of material, making such viscoelastic inserts less resilient, and more compressible than the adjacent portions of the third layer. These inserts or pods are spaced from opposing walls of the trays into which they have been inserted. The spacing is selected to allow for the substantial or full expansion and deformity of such pods or inserts without the inserts impinging upon or interfering with the opposing material of the tray. Such pods or inserts additionally are not bonded to the adjacent upper or lower layers located on either side of the third layer, allowing for such pods or inserts to ride freely within each of such trays.

In the preferred implementation, each of the second, third, and fourth layers of such insole have a thickness of approximately 7 mm in the uncompressed state, such that, with a relatively thin woven top cover as the first layer, the total thickness of the inventive force-reducing insole is slightly greater than 21 mm, that is, 4 or 5 mm short of an inch. As such, the insole may be set into an insole-receiving aperture or other sole structure, or may be otherwise integrated into the sole of the footwear, either permanently or selectively removable therefrom.

The lowermost such layer is designed in the preferred implementation to be constructed of an impact absorbing polymeric material, such as PORON XRD, or material which may be otherwise described as made of a high compression resistant material, either open or closed cell foam, plastic, or rubber. The material of this layer provides a significant reduction in force, as well as adding structure to the insole and allowing for an interface with the devices in which the inventive insole may be used, whether shoes, boots, braces, or casts. For this reason, such bottom layer is useable either above and adjacent to an outsole, or such bottom layer itself may be formed to have a bottom surface suitable for contacting the ground and thus serve as an outsole.

Such top layer of the force-reducing insole in the preferred implementation is designed to be constructed of a cover material that is friction-reducing, water resistant, and antimicrobial, typically a woven material that can be made of several different fabrics, natural materials, or plastic. As such, the top layer is designed to be in contact with the foot, such that overlying additional layers could be inserted by a user if desired, but are not required.

Another implementation relating to the multi-layered insole disclosed herein is based in part on teachings from the applicant's earlier U.S. Pat. No. 11,006,693 entitled Articles of Footwear for Inhibiting and Treating Injuries, specifically the implementation of the insole of the present disclosure into a protective boot as described in said Patent.

Other objects, features and advantages of this disclosure will become apparent from consideration of the following detailed description and from the accompanying drawings, in which:

BRIEF DESCRIPTION OF THE DRAWINGS

FIG. 20 is a table showing physical properties of a material suitable for use with the protective, force-reducing insole of the current disclosure;

FIG. 21 is a table of physical properties of another material suitable for use with a protective, force-reducing insole of the current disclosure;

FIG. 22 is another table of physical properties of another material suitable for use with a protective, force-reducing insole of the current disclosure;

DETAILED DESCRIPTION

As used herein, the terms ambulatory protective device, CAM walker, and walker may be used interchangeably with each other and, accordingly, each and any of such terms shall broadly mean any number of protective boots, walkers, or other lower extremity footwear for controlling or limiting relative movements of a lower extremity, protecting or isolating such lower extremity, or achieving other therapeutic goals related to the lower extremity. The terms distal and proximal, anterior and posterior, medial and lateral, shall be in reference to a standing individual.

Figure 1:
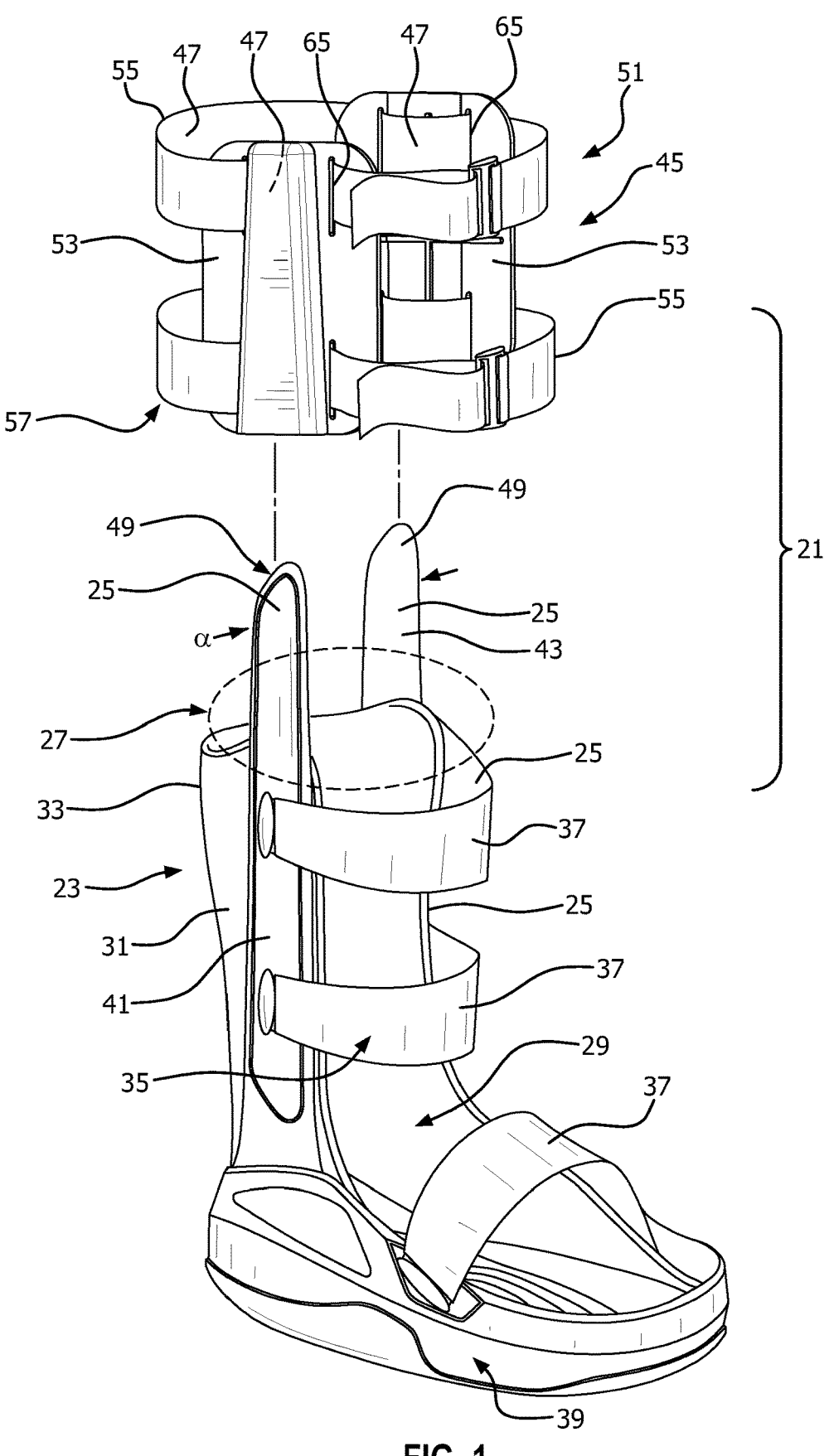
FIG. 1 is a perspective view of one possible implementation of a walker, such as a CAM walker, having a collar assembly which is removably attached to an underlying frame.

Referring more particularly to the drawings, FIG. 1 shows a perspective view of a walker 21 which is manually fittable to and removable from a lower extremity to be treated. In the illustrated embodiment, walker 21 is in the form of a CAM walker configured so as to be suitable for use with a brace device being worn by a patient, such as a cast, on his or her lower extremity. To that end, walker 21 includes a frame 23 which is not only adapted to control ankle movement of a lower extremity received thereon, but is also sized and shaped to receive both the patient's ankle and the associated brace device therein. To that end, frame 23 includes frame elements 25 which at least partially define a frame circumference 27 and a corresponding frame volume 29.

Frame elements 25 may assume a variety of configurations, including, for example, a rigid or resiliently flexible shell 31 having a posterior brace portion 33, a closure system 35, including one or more adjustable closure belts 37, a foot bed 39, and rigid or semi-rigid struts 41 extending upwardly or proximally (in relation to the wearer) from foot bed 39 on each of the lateral and medial sides of the foot bed. Struts 41 are transversely spaced by a distance a at their upper ends so as to have inner surfaces 43 proximate to opposing surfaces of the brace device (such as a cast) when worn on the lower extremity received in walker 21. Walker 21 as described herein is adaptable and suitable for use with any number or type of brace devices, whether rigid or semi-rigid casts of plaster, fiberglass, or alternate materials, splints, bandages or other removable bracing, and the like.

As such, frame 23 has an upper or proximal end adapted to operatively engage portions of the calf when received therein and a lower or distal end adapted to operatively engage portions of the foot, meaning to contact, directly or indirectly through the brace device, in order to protect, restrain, or otherwise control movement of the lower extremity for desired therapeutic purposes.

Figure 2:
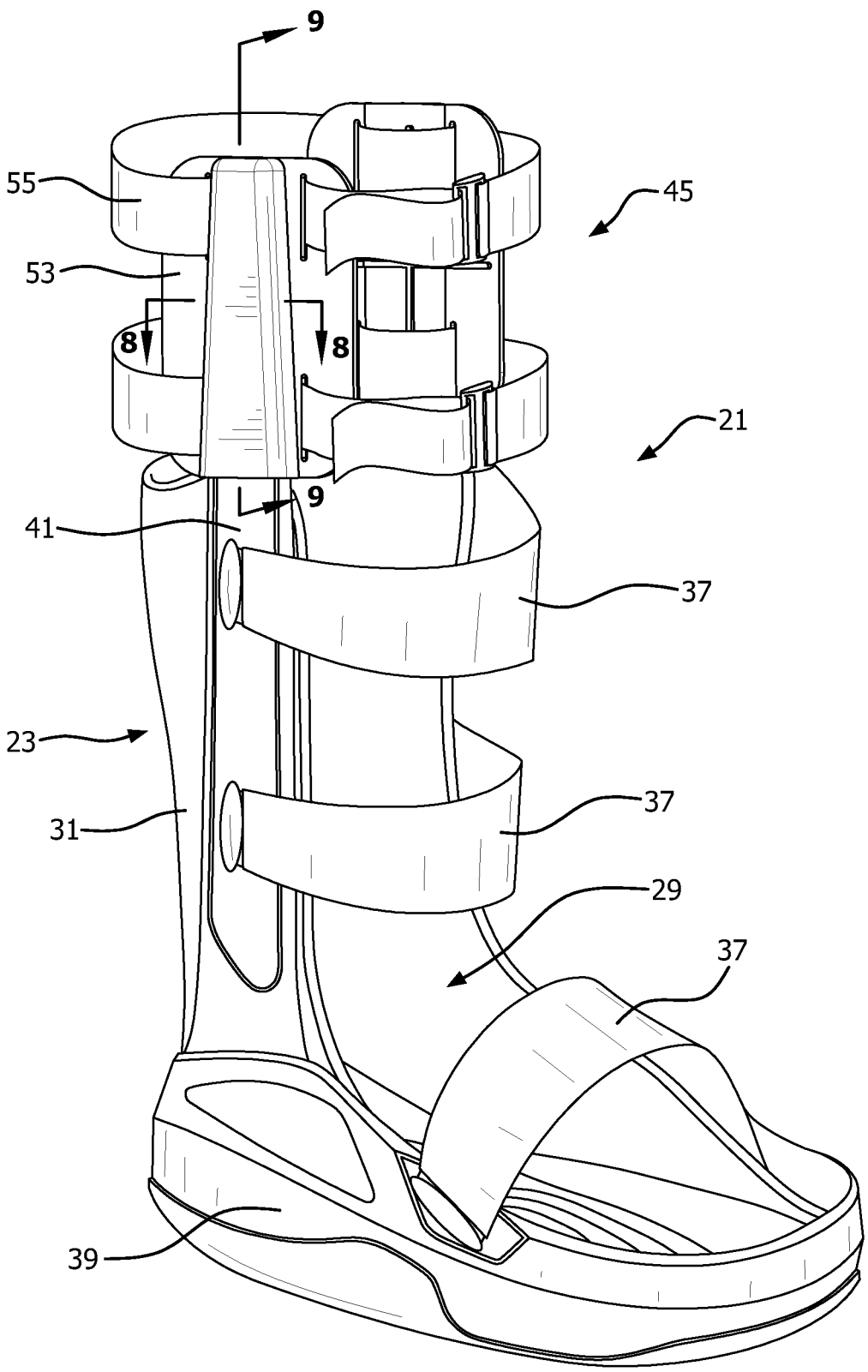
FIG. 2 is a perspective view of the walker of FIG. 1, with the collar assembly removably secured thereto.
Figure 5:
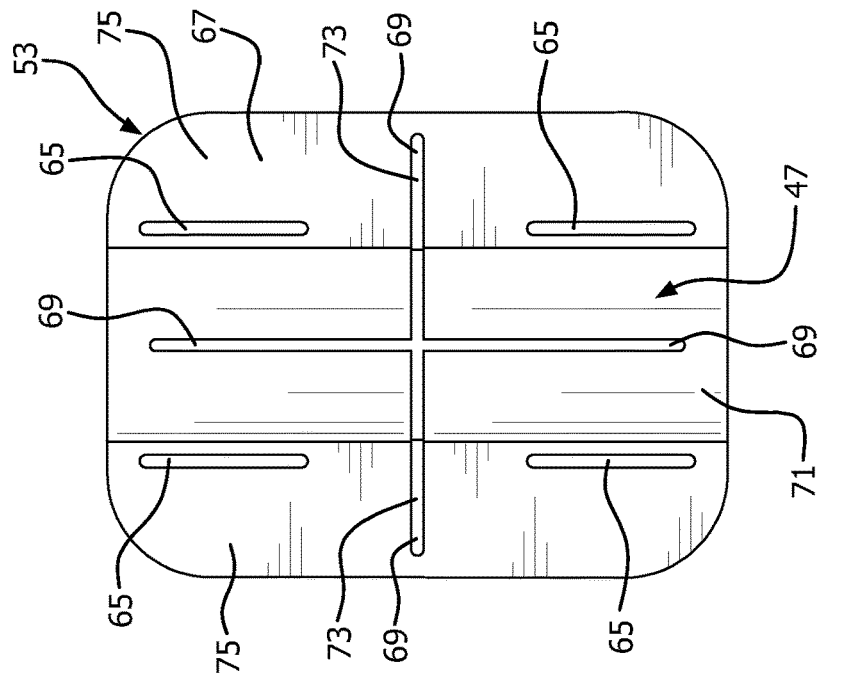
FIG. 5 is a rear elevational view of the portion of the collar assembly shown in FIGS. 3 and 4.
Figure 4:
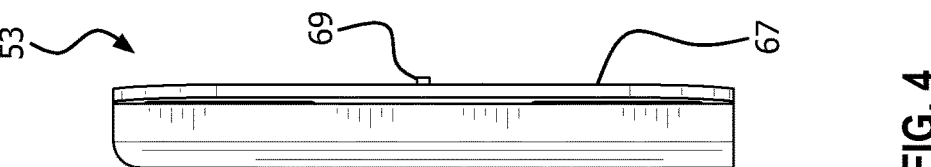
FIG. 4 is a side elevational view of the portion of the collar assembly shown in FIG. 3.
Figure 3:
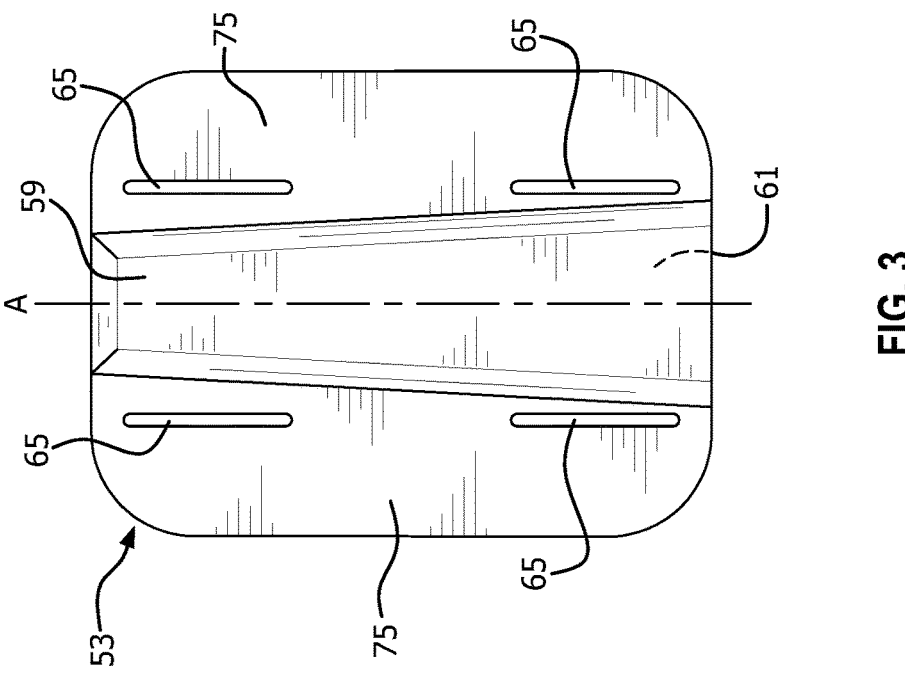
FIG. 3 is a side elevational view of a portion of the collar assembly of FIGS. 1-2.
Figure 6:
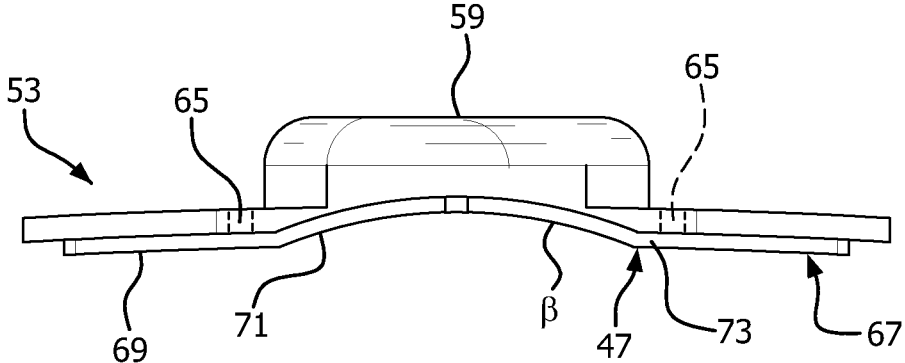
FIG. 6 is a top plan view of the portion of the collar assembly shown in FIGS. 3-5.

In the disclosed and illustrated implementation, a collar assembly 45 is configured as subsequently detailed herein, so as to be selectively fittable to, and manually separable from, the proximal end of frame 23. FIG. 1 shows collar assembly 45 separated from frame 23, whereas FIG. 2 shows collar assembly 45 fitted to such frame 23. More particularly, collar assembly 45 is removably received on upper ends 49 of struts 41. Collar assembly 45 includes one or more engagement areas 47 oriented and suitably configured so that when collar assembly 45 has been fitted to upper ends 49 of struts 41, engagement areas 47 engage an opposing surface of the cast or other brace device received on or into frame 23.

Engagement area 47 may comprise inner surfaces of corresponding engagement members 53, and such engagement members 53 may assume any number of suitable forms, in the illustrated embodiments shown as paddles having quadrilateral profiles. Engagement members 53 are suitably interconnected or secured relative to each other by one or more adjustable, flexible straps 55 which make up a collar closure system 57 which can be manipulated to open or otherwise transform collar assembly 45 so it can surround the cast or other brace device associated with leg walker 21, and then adjusted, such as by tightening or shortening straps 55, thereby transmitting radially inward force on engagement area 47 of engagement members 53. Closure system 57 and associated straps 55 are oriented and sized so that manual tightening or other similar adjustment may produce sufficient inwardly directed force to substantially maintain the engagement of collar assembly 45 with the opposing portions of the cast during the anticipated gait cycle associated with the lower extremity and thereby impart to the patient all the advantages of such engagement.

Figure 7:
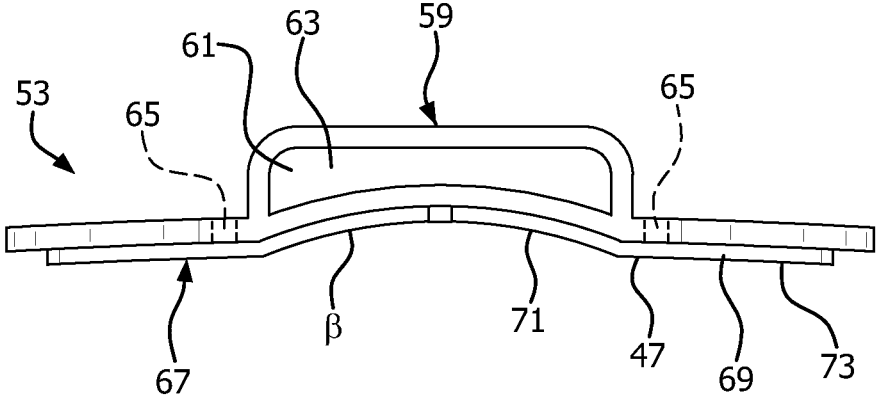
FIG. 7 is a bottom plan view of the portion of the collar assembly shown in FIGS. 3-6.
Figure 8:
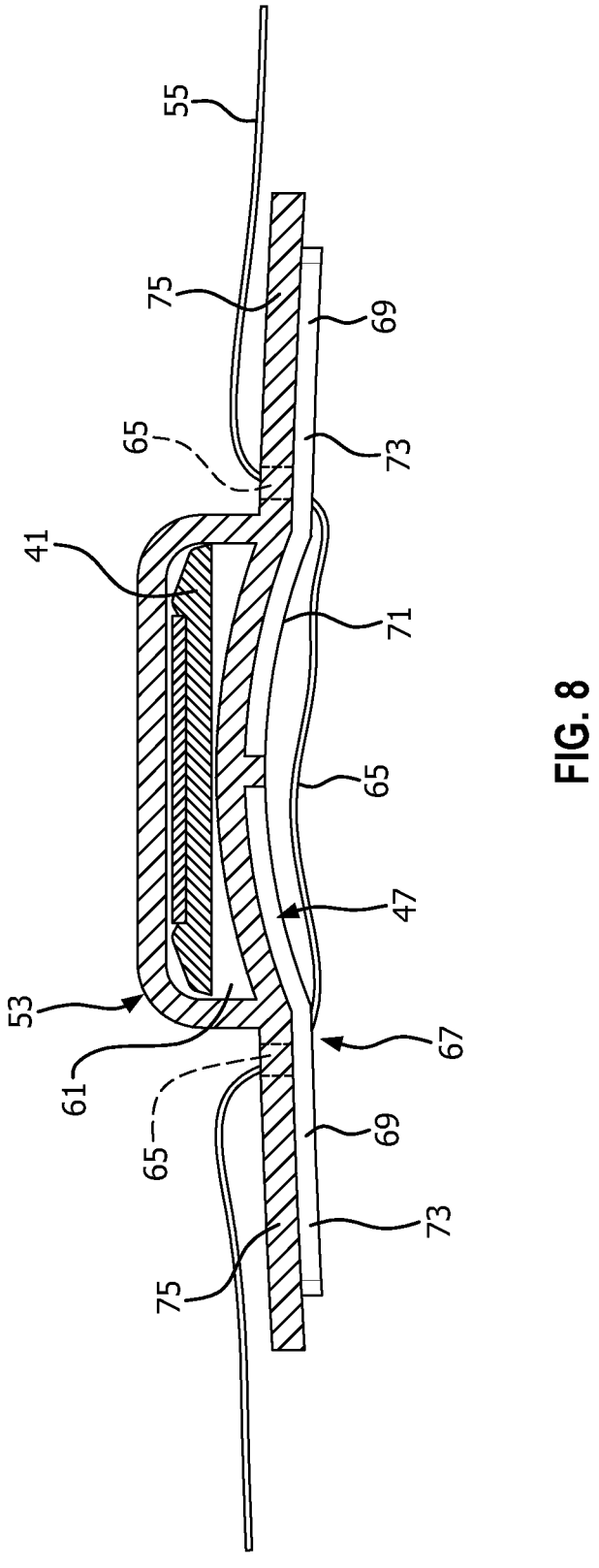
FIG. 8 is a sectional view taken along reference line 8-8 of FIG. 2.
Figure 9:
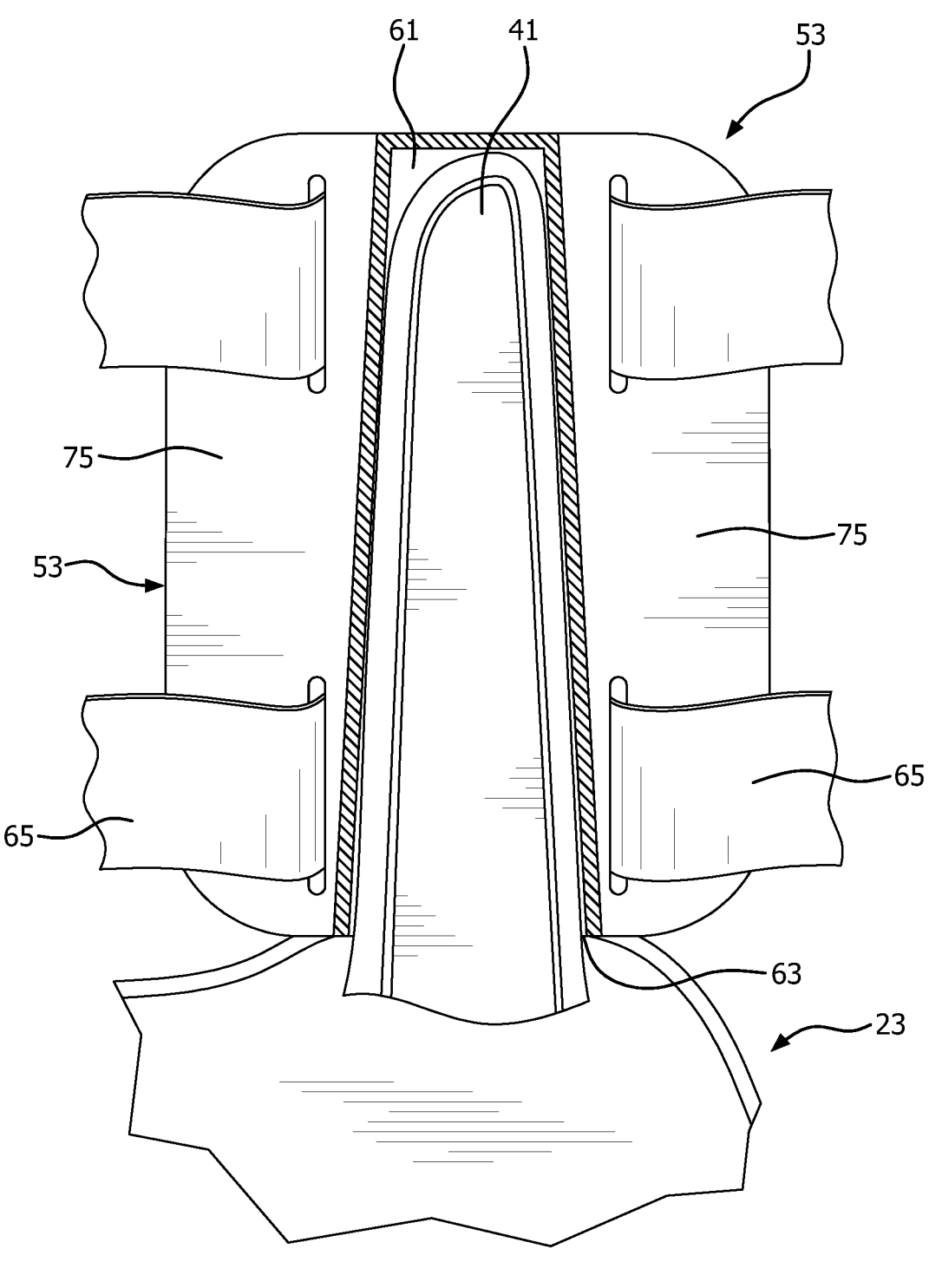
FIG. 9 is a sectional view taken along reference line 9-9 shown in FIG. 2.

Referring now to FIGS. 3-7, one of the engagement members 53 is shown in various plan views and described in further detail. Engagement member 53, shown as a paddle in the illustrations, has a longitudinal axis A and longitudinally extending connection portion 59 by which engagement member 53 can be removably secured to a corresponding one of struts 41 by longitudinal movement of connection portion 59 relative to strut 41 and its upper end 49. As best seen in FIG. 7, connection portion 59 is formed with inner surfaces defining a slot 61 which extends longitudinally and terminates in a slot opening 63 oriented distally or downwardly and sized to receive a mating portion of upper strut end 49 therein. Slot 61 and upper strut end 49 may be removably secured relative to each other by friction fit; mechanical interlock, such as with tabs or flanges, or press-fit or release mechanisms; fugitive adhesives, or hooks and eyes (VELCRO). Mating portions between collar assembly 45 and frame 23 may likewise take on different forms than slot 61 and upper strut end 49, including different configurations of male/female attachment or still other removable attachment structures.

Slits 65 extend through inner and outer surfaces of engagement member 53 so that corresponding straps 55 may be threadably received therethrough for operation as closure system 57 (FIGS. 1, 2).

Engagement member 53 includes opposite inner and outer surfaces, inner surface 67 being substantially planar but having formed thereon a pattern of protrusions 69 extending from inner surface 67, that is, away from the plane of such surface. When collar assembly 45 is secured to frame 23, protrusions 69 extend inwardly from the plan of inner surface 67 toward the corresponding opposing surface area of the brace device. Protrusions 69 are in the form of elongated elements or ribs 73 as illustrated, but may assume any number of shapes and patterns, including a roughed or stippled surface, a pattern of X's, O's, or the like, or any number of protrusions which terminate in surfaces having sufficiently narrow profiles so as to engage the opposing surface of the cast or other brace device corresponding to the upper surfaces of such protrusions 69. The combination of the area of inner surface 67 and geometries of the pattern of protrusions 69 are tuned or selected to substantially inhibit slippage of frame 23 relative to brace device received therein during ambulatory or other anticipated activity.

Inner surfaces 67 of engagement members 53 also include respective, arcuate, inner surfaces 71 which extend on such inner surface 69 to terminate in anterior and posterior longitudinal side edges and have concave arc β of less than 45°, and preferably have an arc extending between 10° and 30°. Extending from the longitudinal side edges of the arcuate surfaces 71 are engagement wings 75. Engagement wings 75 extend transversely, that is anteriorly and posteriorly, respectively, from the side edges of arcuate inner surface 71 and are formed of resiliently flexible material, with a resilient flexibility. Portions of straps 55 overlie or run along outer surface portions of engagement wings 75 so that, in response to straps 55 being adjusted or otherwise tightened and transmitting radially inward force, an inward force on outer surfaces of engagement wings 75, in turn, urges engagement wings 75 against the opposing surface of the brace device adjacent to collar assembly 45.

In view of the foregoing described structure, inner surfaces 67, including arcuate inner surface 71, inner surfaces of engagement wings 75, as well as inner surfaces of straps 55 (FIGS. 1, 2), together form the previously discussed engagement area 47. In this way, engagement members 53 interconnected by one or more of the straps 55 define a substantially cylindrical volume, which is not only sized to circumferentially receive the brace device therein, but is capable of transmitting radially inward force to the engagement area over substantially all of the 360 degrees of the circumference defined by the cylindrical engagement area 47.

The protrusions 29 which are urged by tightening of straps 55 radially inwardly are selected and configured so as to be suitable for engagement of rigid or semi-rigid cast material or other corresponding surfaces of the brace device received in CAM walker 21, and generally not suitable for direct contact with the skin of lower extremity received therein. By suitable engagement of the brace device by engagement area 47, engagement members 53 extend or lengthen the lever arm created between the distal end of CAM walker 21 and its proximal end. Since the frame 23 is configured to reduce force on the foot during gait as a function of the lever arm of CAM walker 21, the extension of the lever arm by addition of collar assembly 45 to frame 23 further reduces force on the plantar surface of the foot when received in CAM walker 21.

Operations of the walkers 21 described herein are apparent from the foregoing description. A medical practitioner or other user of walker 21 may choose to fit collar assembly 45 to frame 23 in order to achieve certain therapeutic goals. A lower extremity bearing a cast or other brace device is received in walker 21 within the volume defined by frame 23 and the circumferential volume defined by collar assembly 45. Suitable adjustment of one or more straps 55 or other comparable collar closure system caused inner surfaces of collar assembly 45 to define an engagement area 47. Such engagement area 47 is brought into engagement, either directly or indirectly with the brace device to help accomplish the desired therapeutic goal for the lower extremity received in the brace device, one such goal being to substantially inhibit movement of the casted lower extremity relative to walker 21.

In response to other therapeutic needs, CAM walker 21 may be used without collar assembly 45 received thereon, or after having removed such collar assembly 45 therefrom. In such cases, struts 41 and frame 23 may be suitably configured or structured so as to define a volume suitable for receiving a lower extremity without a cast or brace device therein. Suitable padding or other soft goods may be associated with frame 23 so that the volume of frame 23 is adapted to receive a lower extremity without a cast therein. As such, a treatment facility may simplify inventory and associated costs by having a frame 23 suitable for use both with non-casted lower extremities, without collar assembly 45 associated therewith, and with casted lower extremities, in which case collar assembly 45 would be fitted to frame 23.

In addition to the advantages apparent from the foregoing description, fixing the proximal portion of CAM walker 21 by means of engagement area 47 of collar assembly 45 allows the proximal portion of CAM walker 21 and the cast itself to move together in more unified movements during the gait cycle or other activities, limiting relative anterior and posterior movement of the cast relative to walker 21, having a positive effect on the gait pattern of the wearer to decrease undesirable forces on the foot, ankle, and lower leg which would otherwise interfere with therapeutic goals.

As a further advantage, the engagement member 53 enhances the offloading characteristics of leg walker 21, that is, reduces the force experienced on portions being treated by the cast on the lower extremity. As such, the combination of the collar assembly 45 and the frame 23 itself create increased mechanical support compared to either the cast itself, or a standard CAM walker.

The increase in lever arm by the collar assembly 45 along with underlying cast also serves to alter the wearer's gait to a more steppage style, thus distributing force over a larger contact surface area on the plantar surface of the foot. In a related manner, the alteration of gait limits speed and strain rate experienced by the foot and results in engagement of larger thigh muscles to advance the lower leg in gait and control the swing phase speed, thereby decreasing impact of the foot against the ground by virtue of engagement of the cast by collar assembly 45.

In one suitable implementation, foot bed 39 has an outer length (posterior to anterior) overall averaging about 315 mm as an outer dimension, and a medial-to-lateral outer dimension of about 140 mm (all such dimensions expressed herein suitably varying for gender, age, and size). Shell 31 of frame 23 extends upwardly or proximally at lateral and medial, respective locations which may be slightly inward of the outer width of foot bed 39. As such, distance ox may range from about 140 mm (about 5½ inches) to about 114 mm (about 4½ inches). If the lateral and medial frame elements 25 include either struts 41 or semi-rigid or rigid material in shell 31, then corresponding inner surfaces 43 of struts 41 or shell 31 may define an inner diameter reduced by the thickness of such frame elements 25, such inner diameter ranging from about 75 mm (about 3 inches) to about 130 mm (about 5 inches). The frame elements 25 spaced as set out above may be used to define a diameter and thus a frame circumference 27 (FIG. 1) ranging from about 240 mm (about 9½ inches) to about 400 mm (about 15.7 inches). It will be appreciated that the transverse spacing of inner surfaces of frame elements 25, whether as part of shell 31 or struts 41 are selected to be spaced proximate to opposing surfaces of brace devices intended to be worn in the lower extremity, and thus the aforementioned dimensions may be further varied to suit particular applications of this disclosure.

Figure 10:
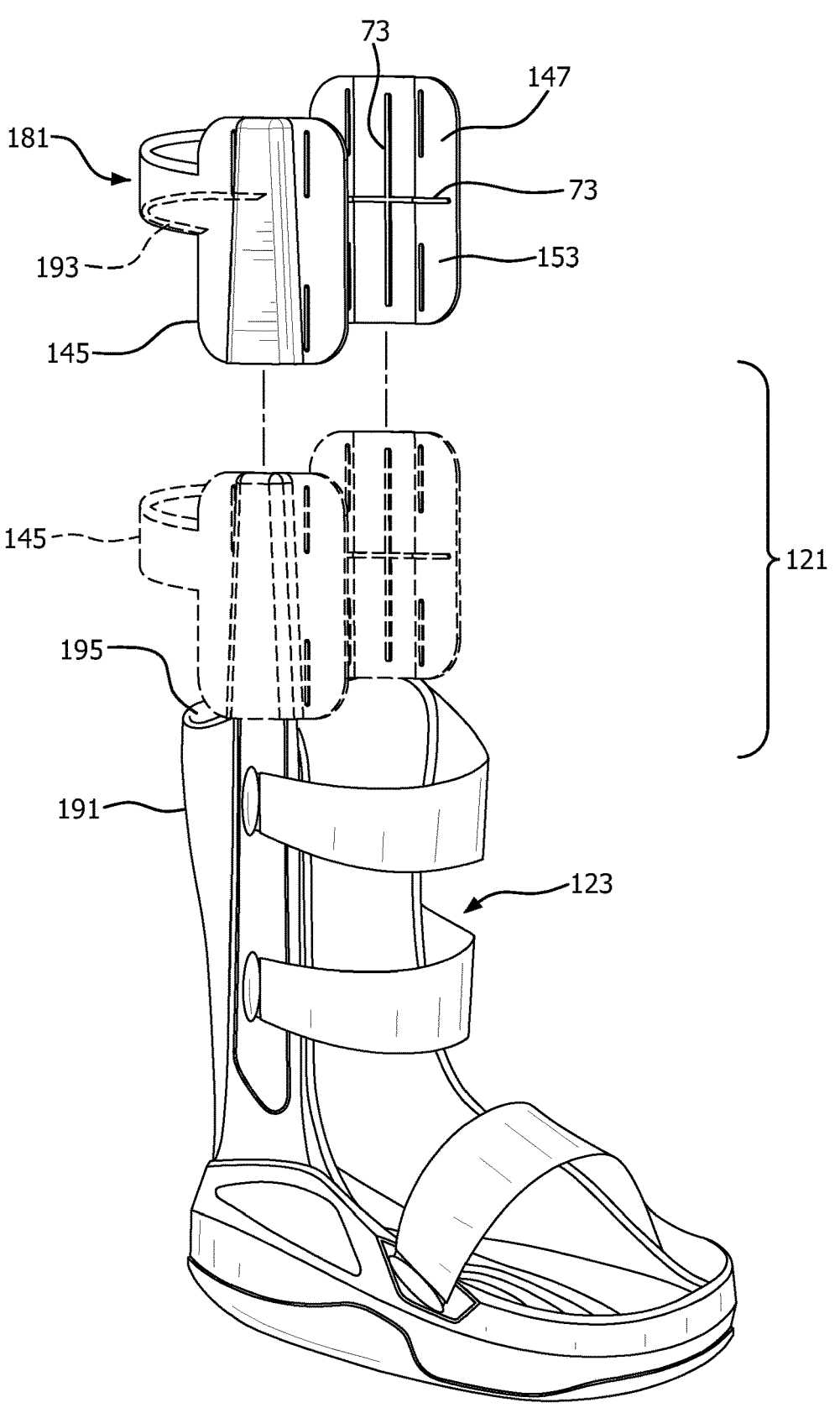
FIG. 10 is a perspective view of another possible implementation of this disclosure.

Proximal end of frame 23, as well as that of frames 123, 223 (described subsequently herein) may extend from a ground plane to corresponding upper proximal edges, such as corresponding to the upper edge of shell 39 below strut end 49 (FIGS. 1-9), or upper edges 195 (FIG. 10), 295 (FIG. 11), by a length ranging from about 230 mm (about 9 inches) to about 330 mm (about 13 inches), such lengths including the height of foot bed 39 and stated as an average height, recognizing that upper edge of frame 23 may be suitably contoured in a case of the illustrated embodiment of frame 23. The lengths of frame 23 may also correspond to the upper ends 49 of struts 41. Given the previously defined values for frame circumference 27 (and associated radii) and the aforementioned ranges in height of frame 23, the frame elements 25 define a corresponding frame volume 29 sized to receive both the ankle and the brace device therein, and ranging in volume from to 1,020 cm$^3$ to 4,380 cm$^3$.

Such dimensions have been found suitable to remain fixed relative to the underlying cast upon manual adjustment of Velcro-equipped straps having dimensions of between 12 mm and 25 mm (½ to 1 inch) in width. Upper ends 49 of struts 41 extend about 127 mm to 178 mm (about 5 to 7 inches) beyond the upper edge of shell 31. As such, if engagement at the upper end of shell 31 by uppermost one of straps 37 defines a lever arm for walker 21 having a first length, the addition of collar assembly 45 on the upper ends 49 of struts 41 increases the lever arm by about 127 mm to 178 mm (about 5 to 7 inches), thereby reducing force on the plantar service of the foot when received in walker 21. Engagement members 53 may be in the form of quadrilateral paddles, as illustrated, extending longitudinally between about 127 mm to 178 mm (5 inches and 7 inches) and transversely between about 100 mm to 152 mm (4 inches and 6 inches). Other sizes and dimensions are likewise suitable, depending on the brace device or other parameters and associated applications of the embodiments herein.

Still further variations are contemplated by this disclosure. Thus, for example, although protrusions 29 are described as engaging the opposing surface area of the cast or brace device received in walker 21, it will be appreciated that engagement area 47 may be equipped with adhesive materials, pneumatic arrangements, such as bladders, other friction inducing materials, hooks-and-eyes (VELCRO), ratchets, and other sorts of adhesive or mechanical affixation devices and materials, suitable for limiting anterior and posterior motion of the proximal end of leg walker 21 relative to the cast received therein.

Collar assembly 45 may likewise assume different configurations than the quadrilateral paddles shown here. For example, referring now to FIG. 10, another possible implementation has a leg walker 121 with removable collar assembly 145 including a posterior portion 181 formed of suitable resiliently flexible material to constitute or enhance a posterior brace and its associated functions on leg walker 121 and may likewise serve to interconnect lateral and medial paddle portions of engagement area 147 of engagement members 153. The removable attachment of collar assembly 145 shown in FIG. 10 may be accomplished in the manner similar to that described with reference to the implementations show in FIGS. 1-9. In addition, collar assembly 145 and proximal end of frame 123 may be formed so that posterior portion 181 mates with a corresponding posterior brace 191 on frame 123. In one possible version, posterior portion 181 includes a downwardly oriented slot 193, which receives an upper edge portion 195 of posterior brace 191 therein.

In still another possible implementation, a walker 221 includes a posterior ankle-foot orthosis ("AFO") 224 and an anterior AFO 226. Posterior AFO 224 is located to therapeutically engage the posterior portion of the lower extremity by contact through any bracing device therebetween. Anterior AFO 226 is removably secured to anterior locations of frame 223 of walker 221, so as to therapeutically engage the anterior portion of the extremity, such as the dorsum of the foot. The AFOs 224, 226 together form a "clam shell" arrangement. Anterior AFO 226 includes anterior reinforcing stay 228 extending longitudinally, that is, from proximal end 230 of frame 223 to distal end 232 of such frame 223.

Pairs of respective lateral and medial fingers 234 extend transversely from reinforcing stay 228 of anterior AFO 226, the pairs of fingers 234 located at spaced longitudinal locations on anterior AFO 226. Fingers 234 are located, sized, and configured to oppose corresponding portions on frame 223 so as to removably secure anterior AFO 226 relative to frame 223. In this particular implementation, hook-and-eye fasteners are used on opposing surfaces of frame portions 236 and fingers 234, such as fasteners marketed under the name VELCRO.

Figure 11:
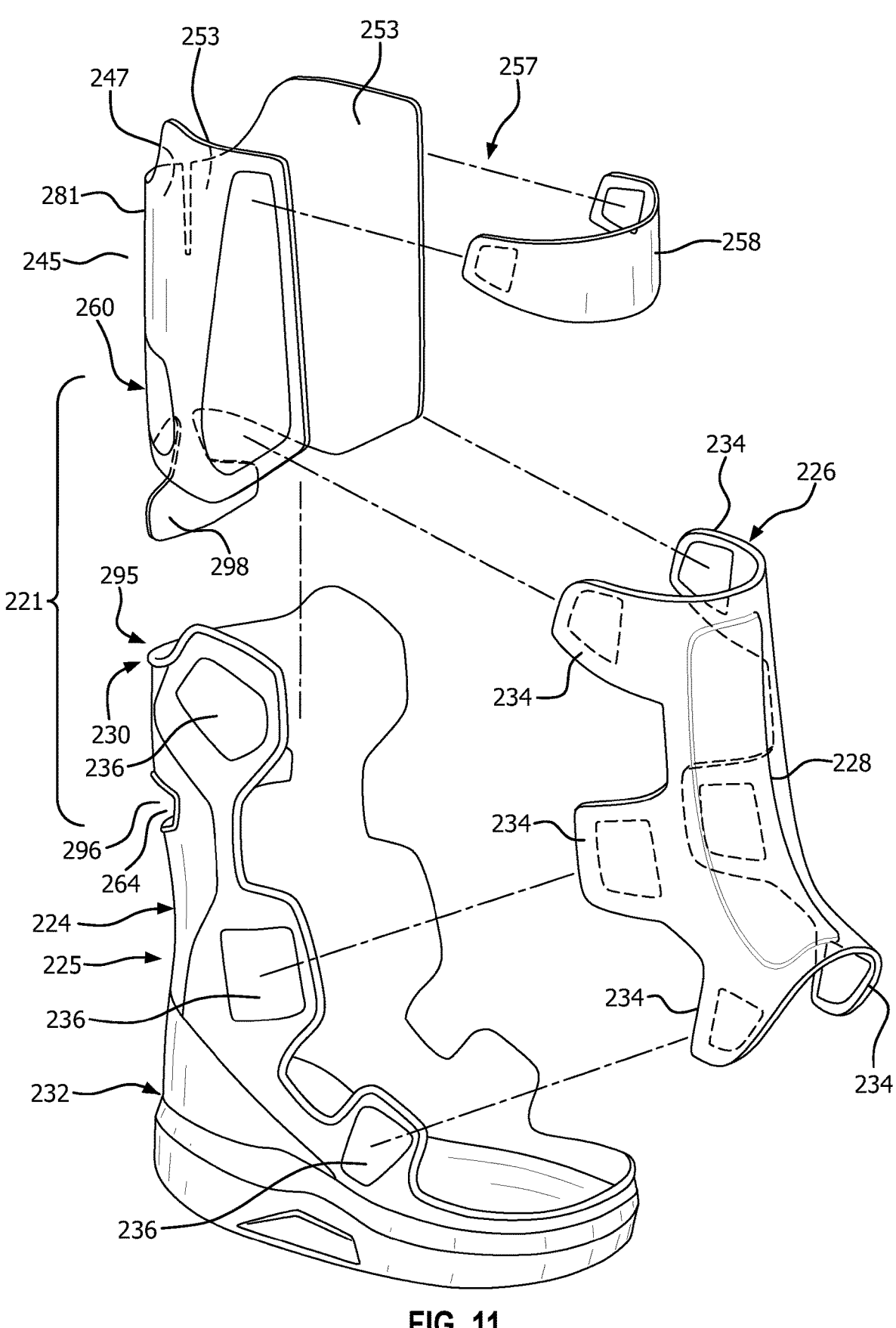
FIG. 11 is an exploded perspective view of still another possible implementation of this disclosure.
Figure 12:
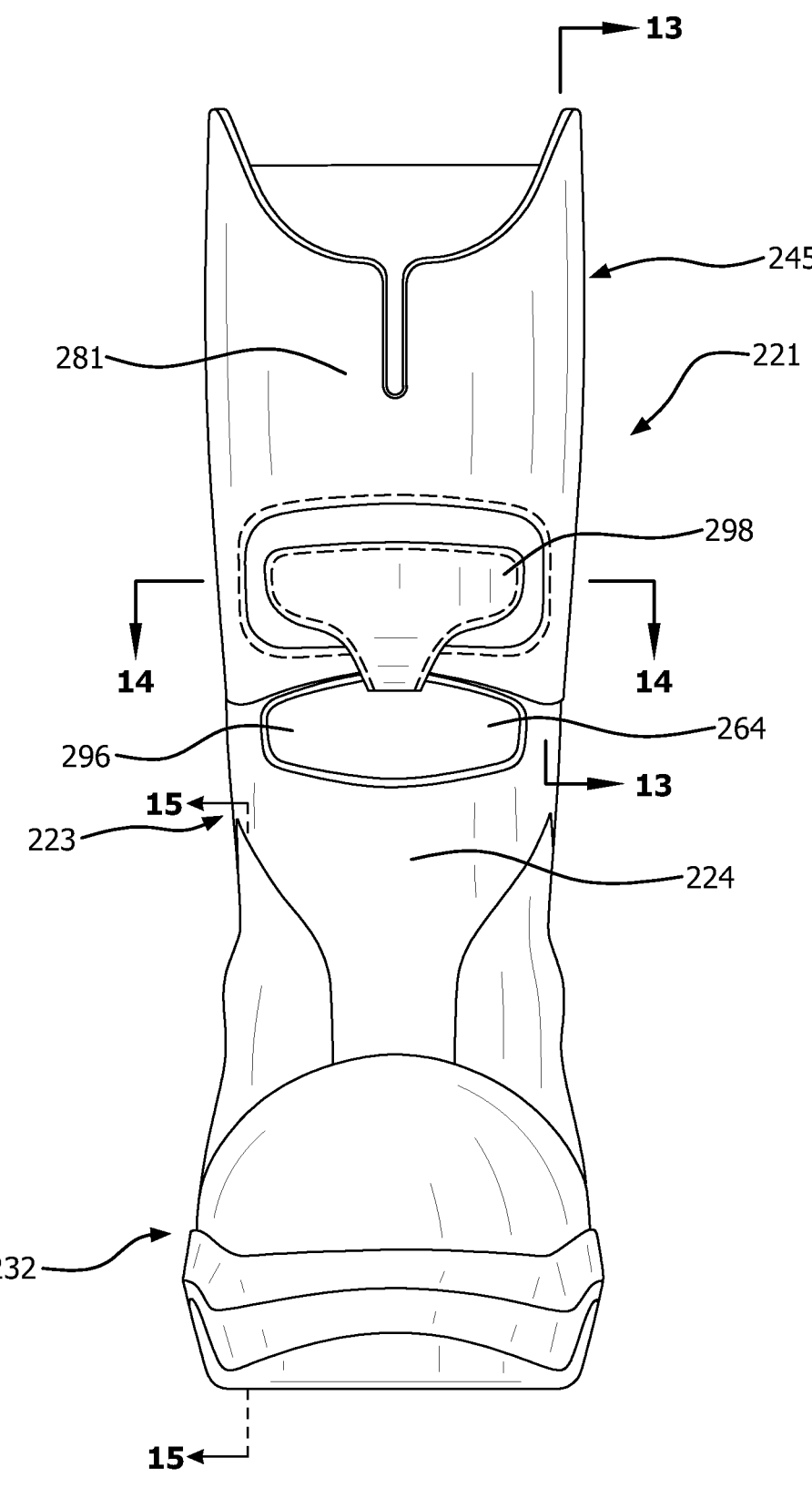
FIG. 12 is a rear elevational view of the implementation of FIG. 11.
Figure 13:
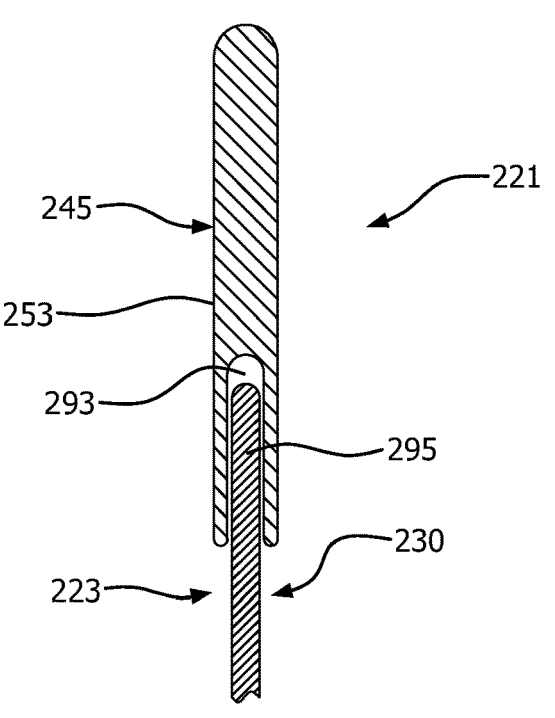
FIG. 13 is a cross-sectional view of the implementation of FIGS. 11-12, taken along line 13-13 of FIG. 12.
Figure 14:
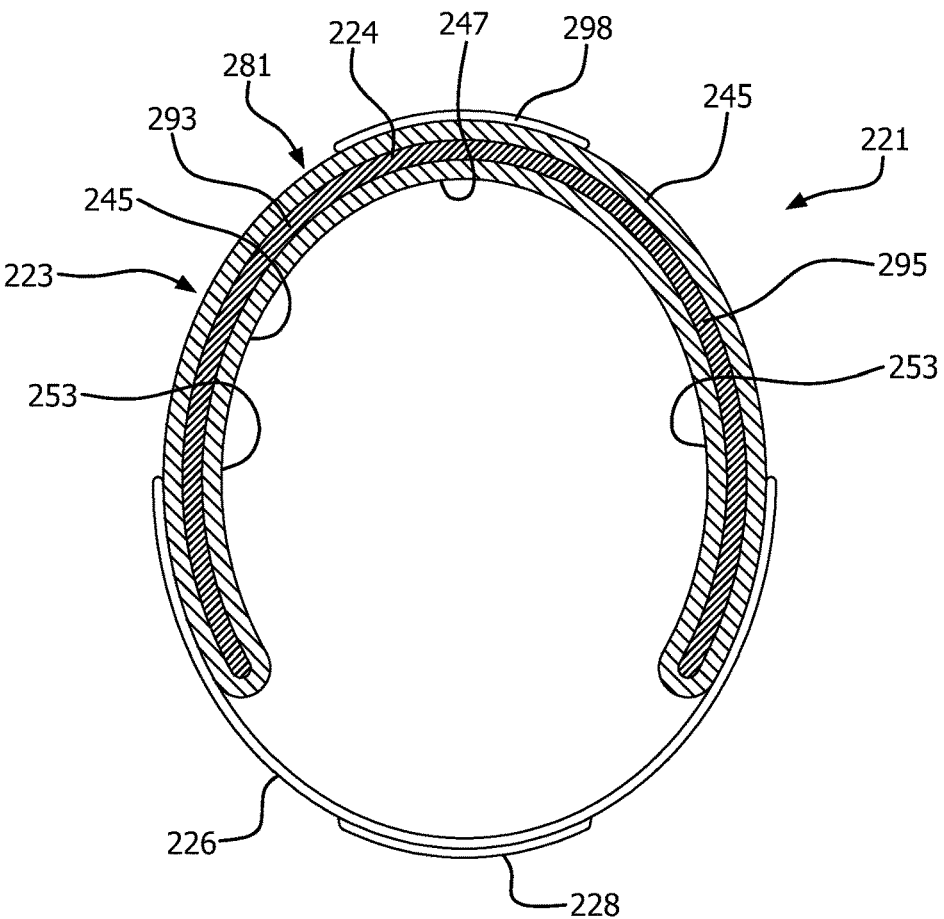
FIG. 14 is a cross-sectional view of the implementation of FIGS. 11-13, taken along line 14-14 of FIG. 12.

Walker 221 may include a removable or selectively fittable collar assembly 245, which operates on principles similar to those discussed with reference to collar assembly 45 and 145. FIG. 11 shows collar assembly 245 removed from frame 223, and FIGS. 12-14 show collar assembly 245 fitted to frame 223, to engage a brace device received in the frame volume defined by frame 223 and collar as discussed previously. In this implementation, collar closure system 257 makes use of a spacer 258 which may be removably secured, such as by hook-and-eye fasteners at its medial and lateral ends, to opposing medial and lateral portions of collar assembly 245.

Collar assembly 245 includes a posterior portion 281. Inner surface of posterior portion 281 may function to engage opposing portions of a brace device received therein and thus constitute one of several potential engagement areas 247. Extending from such posterior portion 281 are lateral and medial engagement members 253, each such members having corresponding inner surfaces which form additional engagement areas 247 for engaging opposing portions of a brace device received within collar assembly 245, as discussed previously in reference to the other embodiments. Engagement areas 247 may or may not include inner surface treatments, protrusions, or other features for enhancing engagement with opposing areas of the brace device received therein.

Collar assembly 245 in this implementation operatively engages opposing portions of the brace device received therein by urging engagement areas 247 radially inwardly and then securing such engagement areas 247 with suitable inward force, in this case with securing spacer 258. Securing spacer 258 extends between medial and lateral sides of collar assembly 245 and is removably secured at locations on the outer surface of engagement members 247.

The distal end portions 260 of collar assembly 245 are formed to define a downwardly oriented slot 293 sized and configured to receive therein upper end portion 295 of frame 223. In this implementation, slot 293 extends substantially around posterior portion 281 as well as the corresponding lower edges of medially and laterally located engagement members 253. The corresponding proximal end of frame 223 extends by a similar circumferential amount to be substantially received in the slot 293 as described.

Slot 293 extends proximally from the distal edge of collar assembly to define a slot depth of any suitable amount for collar assembly 245 to remain fitted to frame 223 and also extend the overall lever arm length of walker 221 if desired for therapeutic purposes. In one possible implementation, collar assembly 245 has an average (longitudinal) length of about 127 mm to 178 mm (5 to 7 inches), and slot 293 extends proximally, inwardly, along such length by amounts ranging from 20% to 70% of the collar assembly length. This results in engagement areas 247 of collar assembly 245 extending proximally beyond the upper (proximal) end 230 by corresponding amounts and extending the length of the lever arm created by walker 221 accordingly. For lever arms of walkers 121, 221 having a first length measured from ground plane to the upper, proximal ends 195 (FIG. 10), 295 (FIGS. 11-14), the dimensions and attachment of collar assemblies 145, 245 may be selected to increase the lever arm to a second length, the second length being longer by 25% to 60%, preferably about 30% to 40%. Other dimensions and configurations of slot 293 and edge portion 295 received therein are likewise suitable. Similarly, locations of slot or other mating portions of collar assembly and frame may be varied, such as by providing edge portion 295 with a slot for receiving an opposing edge (not shown) of the collar assembly 245 therein.

In the illustrated implementation, the proximal end of frame 223 has an aperture 296 formed therein which, among other potential functions, may serve as a handle 264 for manipulating walker 221, such as for fitting frame 223 to the lower extremity or removing it therefrom. Collar assembly 245 includes a tab 298 extending from an inner surface of the collar assembly, such surface located radially inwardly relative to slot 293. In this way, tab 298 is suitably located, dimensioned and configured to be foldable or moved hingedly so as to be selectively manipulatable around the upper edge of handle 264 formed in frame 223. Tab 298 further includes suitable fastening elements, such as hook-and-eye fasteners, so that, once manipulated around upper edge of handle 264, tab 298 may be removably secured to the outer surface of collar assembly 245. In this manner, tab 298 restrains collar assembly 245 from proximal or upward movement relative to frame 223, because upward movement would cause tab 298 and upper edge of handle 264 to engage each other and thus resist proximal or upward movement of collar assembly 245.

Anterior AFO 226, collar assembly 245, spacer 258, and other components of walker 221 may be formed of any suitable resilient, flexible, rigid, or semi-rigid materials, possessing, corresponding reinforcing, resiliency, rigidity, of flexibility characteristics, in accordance with locations of such materials relative to a brace device received therein. Components formed from such materials would likewise have a certain amount of flexibility for purposes of operatively engaging corresponding portions of the lower extremity, either directly or indirectly through the brace device, thereby accomplishing immobilization, offloading, or other therapeutic objectives. As such, certain portions of frame 223 in collar assembly 245 are characterized as "semi-rigid," that is, resiliently flexible, the amount of resiliency and flexibility being tuned to the particular application.

Figure 15:
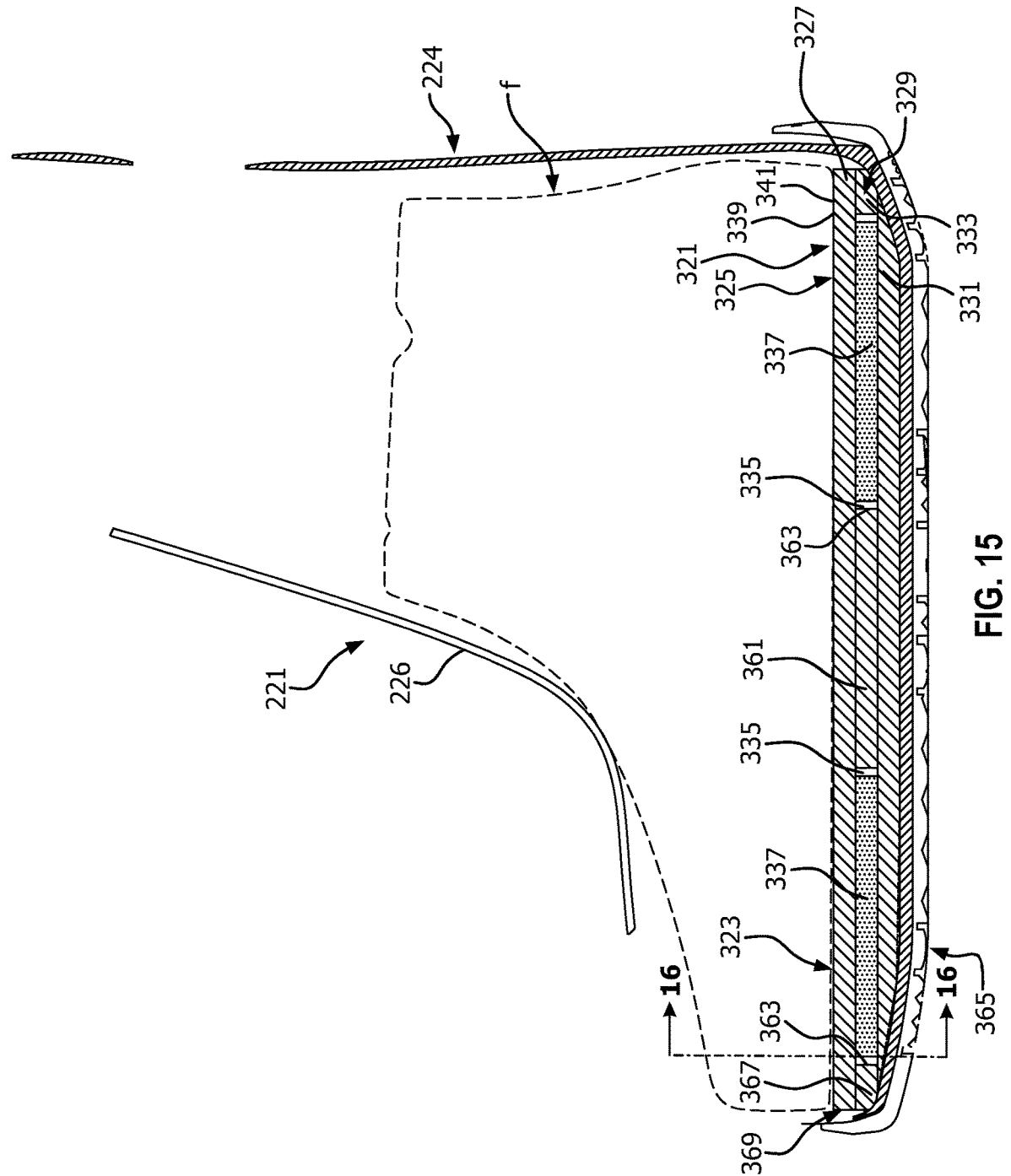
FIG. 15 is a sectional side view, showing portions of another implementation of the ambulatory protective device of FIGS. 11-14, taken along line 15-15 of FIG. 12.
Figure 16:
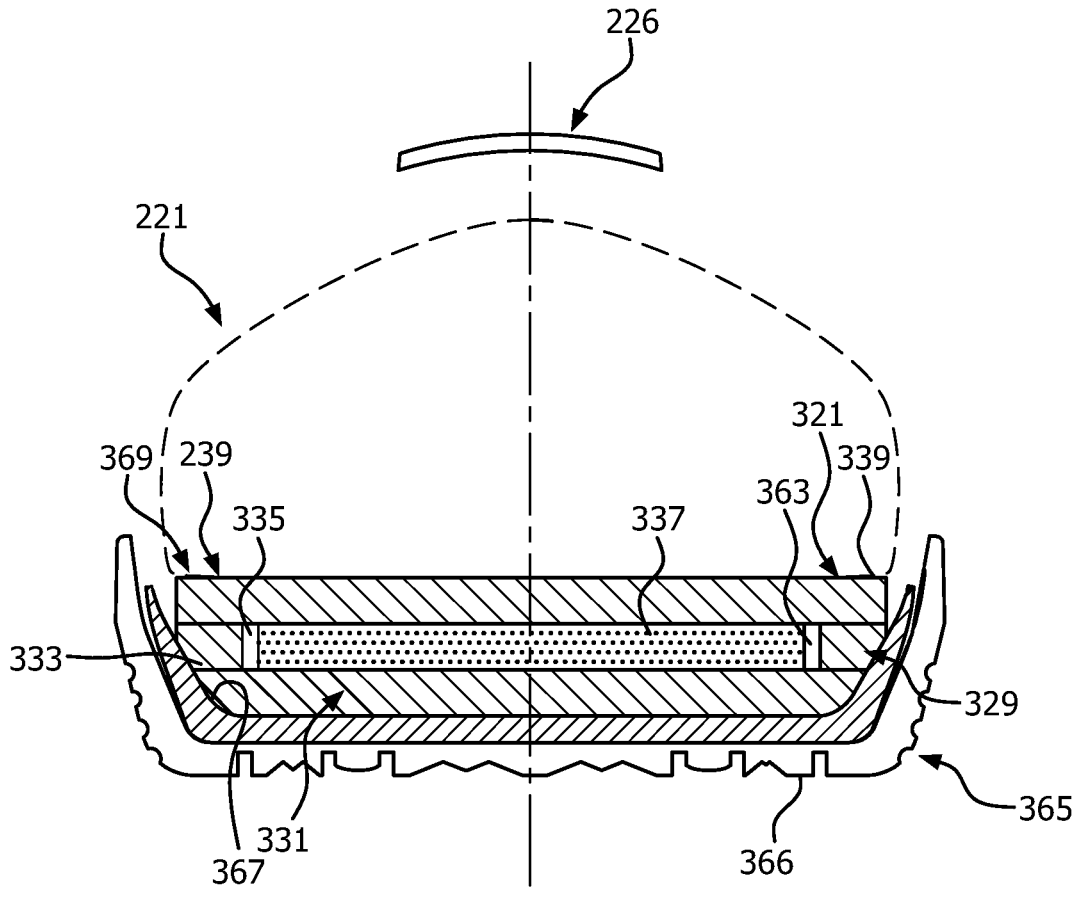
FIG. 16 is a front sectional view of the ambulatory protective device of FIGS. 11-15, taken along line 16-16 of FIG. 15.

FIG. 15 is a sectional side view, showing portions of the implementation of the ambulatory protective device of FIGS. 11-14, taken along line 15-15 of FIG. 12. Walker or ambulatory protective device 221 has a footbed 239 which includes therein an insole 321. Insole 321 and footbed 239 extend medially, laterally, distally, and proximally to underly a person's braced, cast, or bandaged foot f when ambulatory protective device 221 is worn on the lower extremity. Insole 321 and footbed 239 may be thought of as having a forefoot area 323 located thereon, so as to therapeutically or operatively engage the user's forefoot, especially its metatarsal heads. Such metatarsal heads may be the location or locations prone to, or having pain, such as metatarsalgia, wounds or ulcers, or other foot conditions, including without limitation those of diabetics. Footbed likewise has a heel area 325 located and extending in footbed 239 and insole 321 toward the proximal side of the plantar region of the foot, thereby underlying the heel of the wearer and, as in the case of the forefoot area 323, therapeutically or operatively engaging the heel of the wearer, which heel, similarly, may be experiencing or prone to pain, wounds, or other foot conditions.

Referring now to FIGS. 15-18, insole 321 includes a top layer 327, a middle layer 329 located under top layer 327, and a bottom layer 331 located under middle layer 329.

Middle layer 329, in the illustrated implementation, is formed into a stratum 333 having defined therein structures referred to as open trays or chambers 335. Open trays or chambers 335 are located in forefoot and heel areas 323, 325, respectively. In this implementation, stratum 333 consists essentially of polymeric foam material.

Inserts or pods 337 are adapted to be received in open trays or chambers 335. In this implementation, inserts 337 consist essentially of viscoelastic material, it being understood, however, that other polymeric materials may likewise be suitable. It is likewise understood that encapsulating the viscoelastic material in an outer casing is within the definition of such inserts 337 consisting essentially of viscoelastic material.

The viscoelastic material and the polymeric foam material have associated therewith sets of physical properties. In one possible implementation, the viscoelastic material comprises a viscoelastomer or gel having physical properties as set out in FIG. 20. Furthermore, in such implementations, the polymeric foam material of stratum 333 may comprise ethylene vinyl acetate (EVA) having the physical properties set out in the table of FIG. 21. It should be noted that the physical properties are expressed in the tables of FIGS. 20 and 21 both in terms of ISO standards as well as ASTM standards, with associated units for each such standards and related methodologies.

Referring to the tables of FIGS. 20 and 21, the compression set and rebound values associated with the polymeric foam material are higher than the corresponding compression set and rebound values associated with viscoelastic inserts. Those values have been selected to cause insole 321, when worn during ambulation, to reduce the average contact pressure in both the heel area 325 and forefoot area 323, when compared to ambulation without insole 321.

Figure 23:
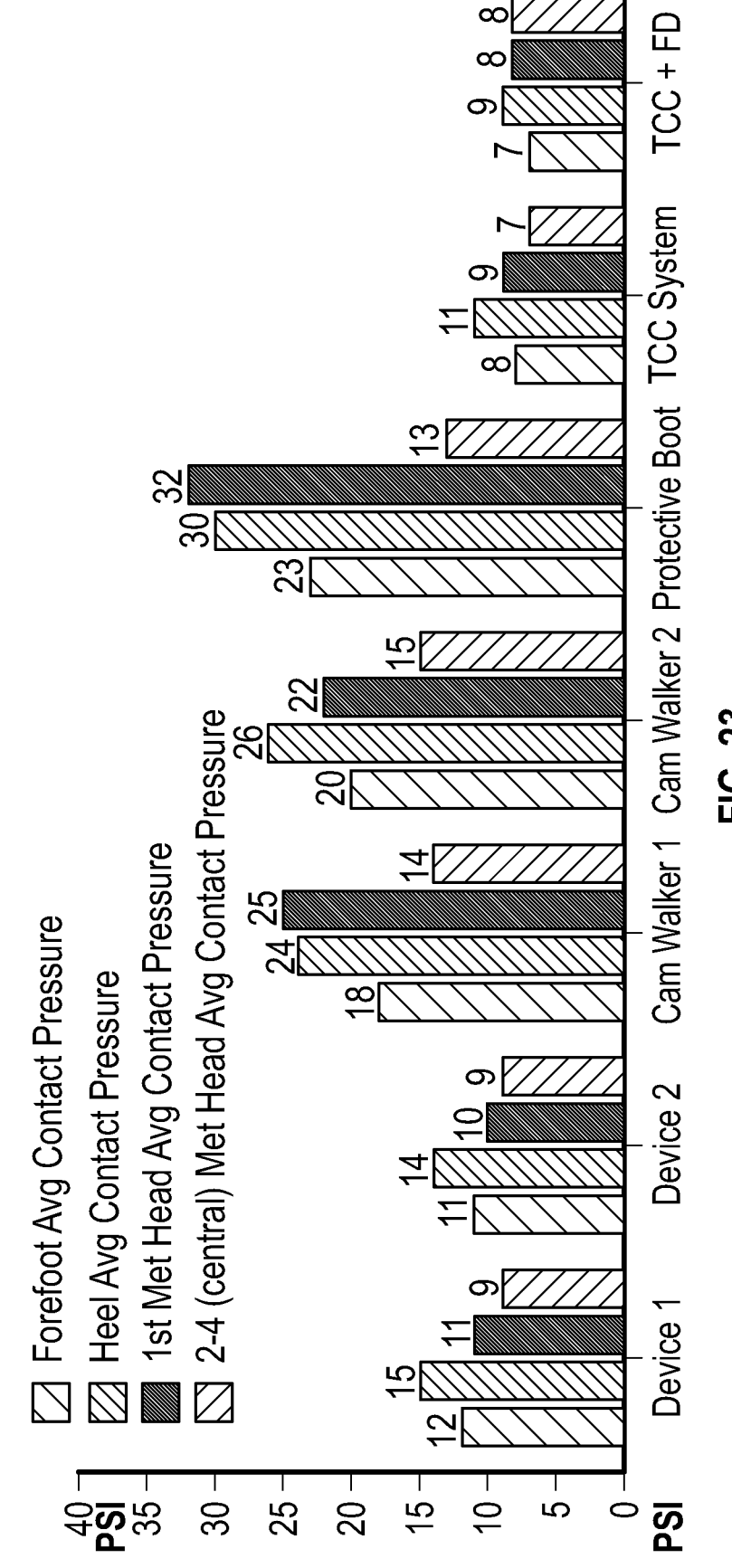
FIG. 23 is a bar graph showing force-reducing characteristics of ambulatory protective devices having the protective, force-reducing insole of the present disclosure, compared to ambulatory protective devices without such protective, force-reducing insole.
Figure 24:
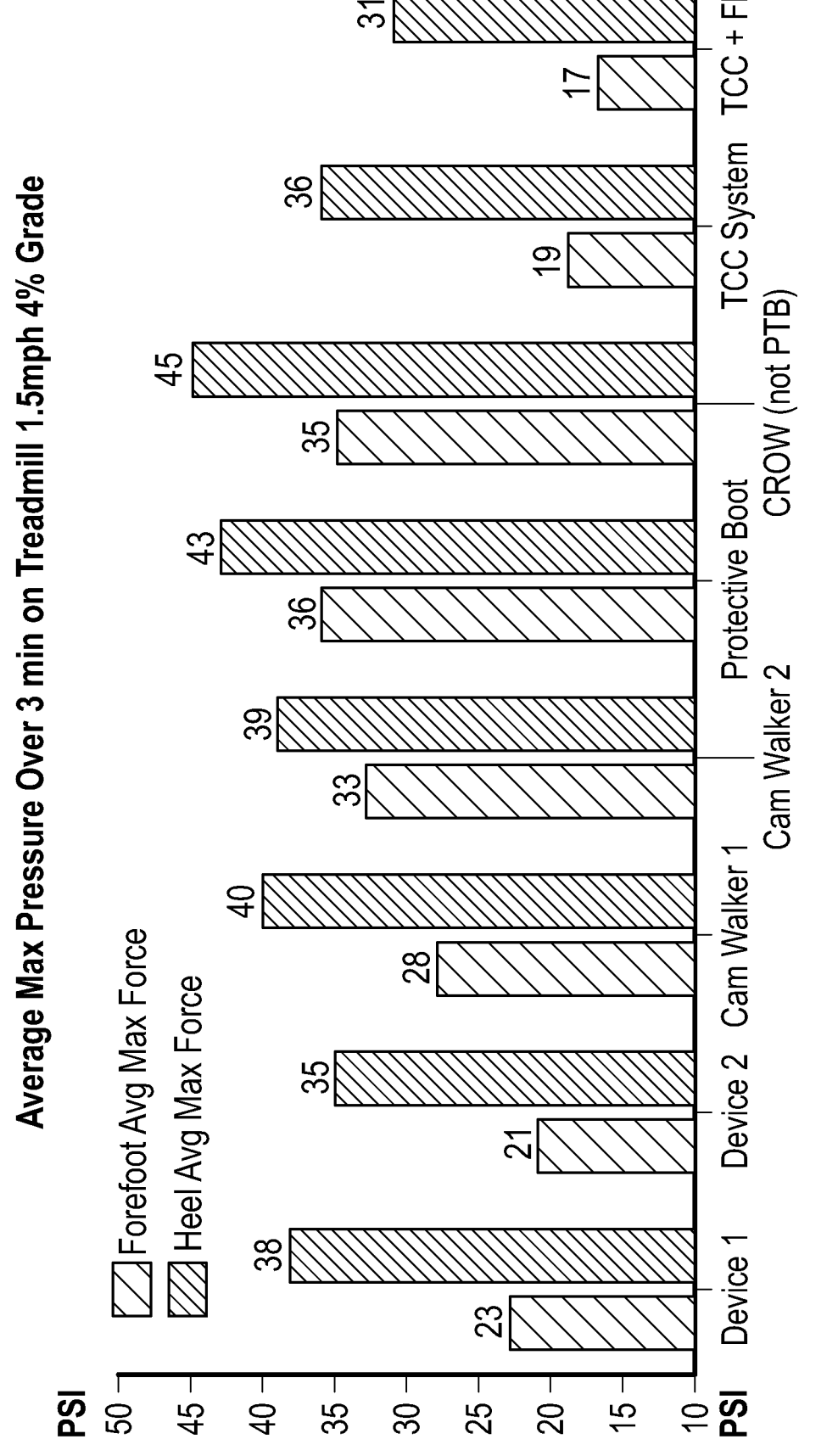
FIG. 24 is another bar graph showing force-reducing characteristics of an ambulatory protective device equipped with a protective, force-reducing insole of the present disclosure, compared to ambulatory protective devices without such protective, force-reducing insole.

The reduction in average contact pressure is further described in the bar graph of FIG. 23. As seen in FIG. 23, average contact pressure of four anatomical areas has been diagrammed, in this case the forefoot, the heel, the first metatarsal head, and metatarsal heads two through four. The contact pressure for each of these four areas has been averaged over a period of three minutes during testing of ambulatory protective device 221 on a size 12 foot of a two-hundred-pound male. The resulting average contact pressures of ambulatory protective device 221 equipped with insole 321 have been compared to the average contact pressures measured for ambulatory protective devices without insole 321 described herein. More particularly, Device 1 of FIG. 23 corresponds to ambulatory protective device 221 (with insole 321), Device 2 corresponds to ambulatory protective device 221 (with insole 321) equipped with collar assembly 245. In contrast, the higher average contact pressures of the remaining five sets of bars correspond, respectively, to (1) a CAM walker without insole 321 nor collar assembly 247, (2) a CAM walker without insole 321 but with collar assembly 247, (3) a protective boot corresponding to a typical CROW Walker, (4) a total contact cast system having cast material in a boot (labeled under the heading "TCC System"), and (5) the cast of item (4) received in ambulatory protective device 221 with insole 321.

Figure 17:
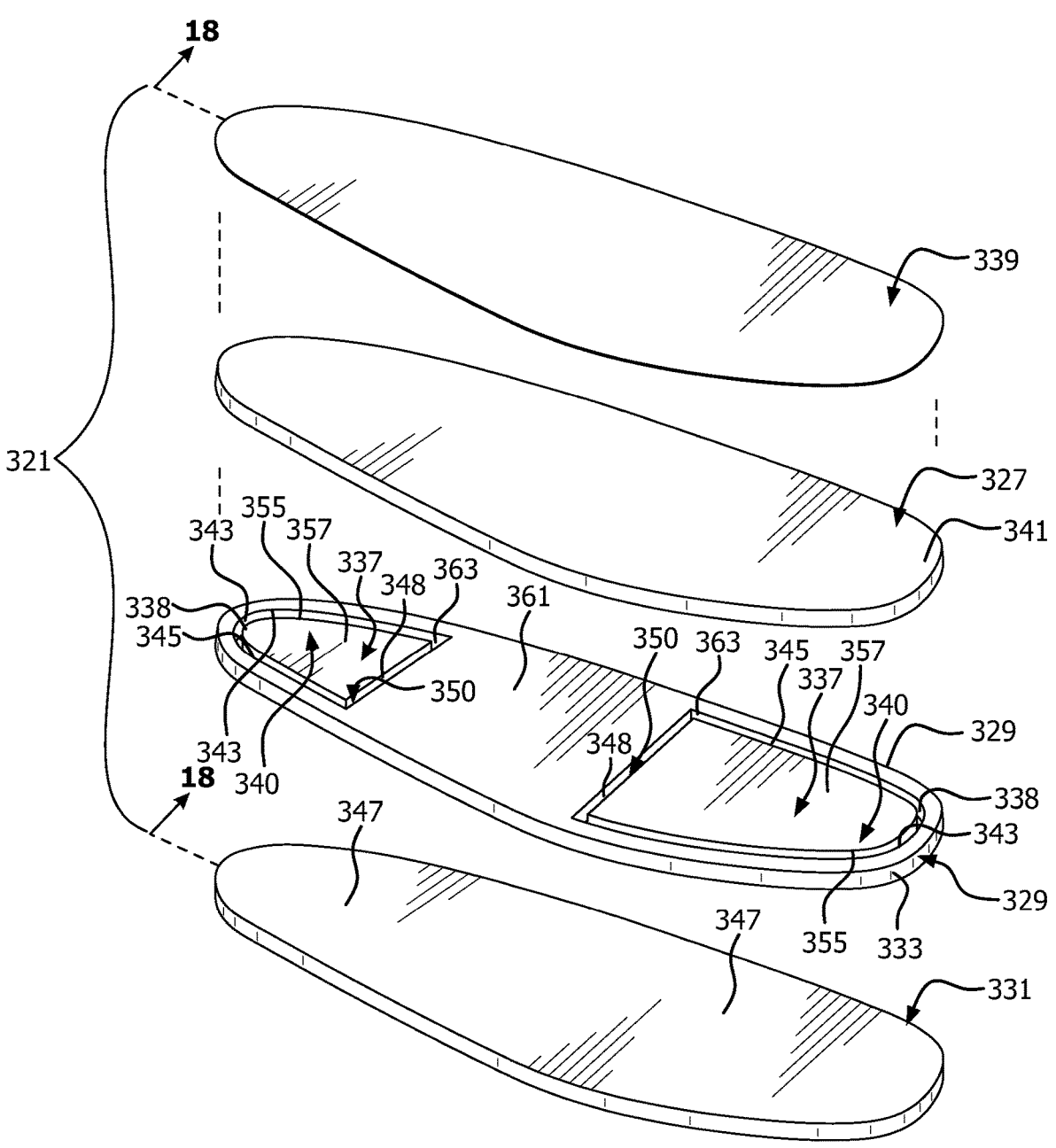
FIG. 17 is an exploded perspective view of one implementation of the protective, force-reducing insole suitable for use with an ambulatory protective device, such as that shown in FIGS. 11-16.
Figure 18:
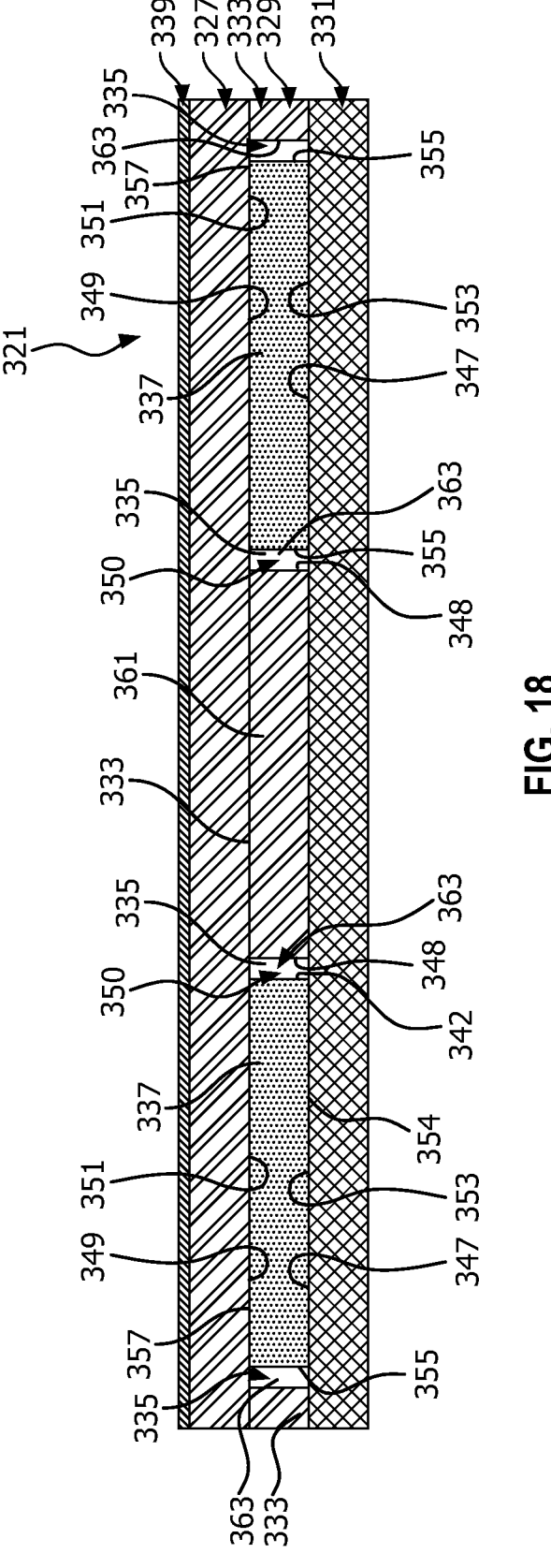
FIG. 18 is a sectional, side view of the insole of FIG. 17 taken along line 19-19 of FIG. 18.
Figure 19:
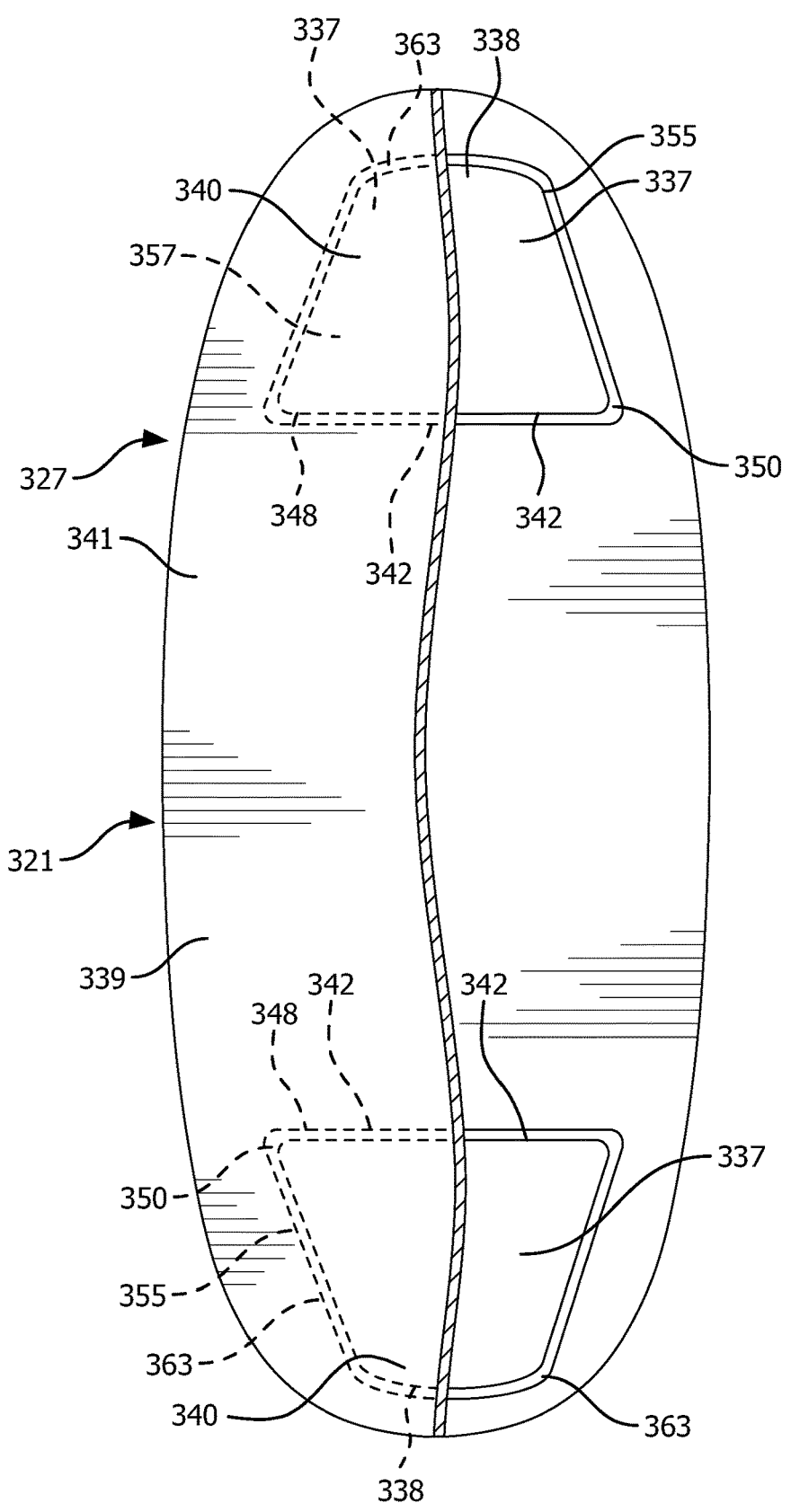
FIG. 19 is a top view of the insole of FIGS. 17-18.

In certain implementations, upper layer 327 of insole 321, as well as stratum 333 of middle layer 329 may be formed of ethylene vinyl acetate (EVA) having physical properties in the ranges shown in FIG. 21. In such implementations, as best seen in FIGS. 17 and 18, inserts 337 have substantially the same thickness as stratum 333 and thus are coextensive with top and bottom surfaces of middle layer 329 when in an uncompressed state. In the implementation illustrated in FIGS. 15-18 and discussed herein, the properties of the viscoelastomeric material of inserts 337 are such that, as seen in FIGS. 20 and 21, the compression set value of the polymeric foam material of stratum 333 may be configured to be 200% or higher than the compression set value of the viscoelastic material of inserts 337. Furthermore, the rebound value of the polymeric foam material of stratum 333 is configured to be at least 800% higher than the rebound value of the viscoelastic material of inserts 337.

Accordingly, from the above, insole 321 is a configuration of differing materials, having associated physical properties, dimensions, and locations, such that, when subject to contact or impact, that is, compressive force, the force or pressure measured at the time of application of such contact or impact pressure is reduced in the heel area 325 and the forefoot area 323 for those periods of time during the gait cycle when the device 221 with insole 321 on the wearer's foot contacts the ground. Such periods of time during which the foot contacts the ground are generally referred to as the stance phases of gait cycles. Accordingly, contact or impact pressure reduction from device 221 equipped with insole 321 extends over a period of time corresponding to the stance phase, with corresponding therapeutic benefits to the overlying foot of a wearer. It will be appreciated that the quantitative time periods for gait cycles and stance phases will extend over a certain range of values known to those of skill in the art, and that such time values depend on several variables, such as the physical characteristics of the wearer, the associated activity, and foot conditions present.

The selected physical properties set forth in FIGS. 20-23 for layers 327, 329, 331, and stratum 333 and inserts 337, include durometer values as just one of many physical properties which have been combined to produce the ambulatory protective device 221 and its insole 321 described herein.

In certain implementations, the durometer value associated with the polymeric foam material of stratum 333 and the durometer value associated with the viscoelastic material of inserts 337 are selected to vary from each other within a range of 63% to 90%. In one suitable implementation, durometer of the polymeric foam material of stratum 333 ranges between 24 and 30 whereas the durometer of the viscoelastic material of stratum 333 ranges from 32 to 38, both values measured using the Shore C scale under the SATRA™ 205 methodology.

Layers 327, 329, and 331, and stratum 333 and inserts 337 likewise have been configured so that viscoelastic inserts, in one possible implementation, have a viscosity ranging from 350 centipoise to 450 centipoise, whereas the polymeric foam material of stratum 333 is non-viscous.

Referring again to FIGS. 11-15, insole 321 of ambulatory protective device 221 comprises a cover layer 339 secured to top surface 341 of top layer 327. Cover layer 339 is generally thin, meaning having a height which is relatively less than layers 327, 329, and 331, preferable being in the range of 0.5 millimeters to 2 millimeters, and comprised of woven material suitable for more directly engaging the lower plantar surface of the wearer's foot, whether directly, such as through a sock, sleeve, or webbing, or indirectly through a bandage or other indirect contact. Accordingly, cover layer 339 may be configured to be friction reducing, water resistant, and antimicrobial. As such, insole 321 and its layers 339, 327, 329, and 331 may be configured to extend over substantially all of footbed 239 and thus insole 321 may be thought of as comprising four, substantially planar strata.

Bottom layer 331 may be formed from a variety of suitable polymeric materials. In this implementation, bottom layer comprises a polyether, that is, a polyurethane material having physical properties set out in the ranges shown in the table of FIG. 22. In certain implementations, bottom layer 331 may comprise or consist essentially of the polymeric foam material marketed under the trademark PORON XRD. In one suitable implementation, the compression set and rebound values of bottom layer 331 are greater than or equal to the corresponding compression set and rebound values associated with the polymeric foam stratum 333 of middle layer 329. For example, compression set value of bottom layer 331 may be between 40% and 60%, a rebound value may be between 37% and 47%, as set out in FIG. 22, whereas the compression set value of the ethylene vinyl acetate of stratum 333 may range from 20% to 40%, and the rebound value between 41% and 51%.

In further implementations, measuring with the Shore C hardness scale associated with medium hard materials, the polymeric material of top layer 327 may comprise the aforesaid polymeric foam, but may likewise comprise medium hard rubber, elastomers, or thermoplastic, among other polymeric materials, and is formed to have a durometer of 25 C to 30 C±3 C, and with an average or constant thickness of 7 mm. Stratum 333 may be formed similarly, and have similar thickness, except for trays or chambers 335. Other durometers, and physical properties other than those employed in the described implementation herein, or as set out in the tables of FIGS. 20-22, are likewise within the scope of this disclosure. For example, inserts 337 may have durometer values ranging between 10 C to 55 C on the Shore C scale.

Layers 327, 329, 331, and top cover layer 339, as well as stratum 333, may have constant thickness or varying thicknesses, depending on the application. Layer 327 has a lower surface with locations thermally bonded or affixed to portions of opposing surface of layer 329 underlying layer 327, such as with an adhesive.

In certain implementations, middle layer 329 is a foam, open or closed cell, and of medium density, such as between 0.16 to 0.20 g/cm³ (approximately 11 lbs/ft³), and a medium durometer, such as between 22 C and 33 C.

Inserts 337 may be constructed of viscoelastic material, such as gel, but may likewise comprise or consist essentially of materials including, but not limited to, urethane polymers, silicone polymers, rubber polymers, and cyanoacrylate polymers. Inserts 337, as illustrated, have respective, hemispherical shapes 340 (FIG. 17), extending to terminate in arcuate or ovoid edges 338 from linear edges 342, the arcuate edges 338 being located at proximal and distal locations of footbed 239 and linear edges 342 being interior to such arcuate edges 338. Other shapes and configurations of inserts 337 may likewise be suitable. While inserts 337 are located in heel and forefoot areas 323, 325, other variations of the illustrated implementation may employ only one of the inserts 337, located in a corresponding one of the forefoot and heel areas 323, 325, and such one-insert embodiments are likewise within the scope of this disclosure.

Trays or chambers 335 are bounded by circumferential walls 343 which define sides 345 of trays or chambers 335. Chambers 335 are further bounded by overlying and underlying planar polymeric foam portions 349, 347, respectively, to define respective tops 351 and bottoms 353 of chambers

335. As such, sides 345, tops 351, and bottoms 353 define corresponding tray volumes bounded by such structures. Viscoelastic inserts 337 likewise extend to outer edges 355 and upper insert surfaces 357 and lower insert surfaces 359.

In the illustrated implementation, linear edges 342 of inserts 337 coextend with opposing linear portions 348 of walls 343 of the chambers or trays 335. The linear portions 348 are spaced proximally and distally from one another to define a central portion 361 on stratum 333. As such, linear edges 342 represent the furthest inward or proximal location of viscoelastic material of inserts 337 and form respective boundaries 350 between the viscoelastic material of inserts 337 and the non-viscous, polymeric foam material of the central portion 361 of stratum 333. The differing physical characteristics present on either side of boundaries 350 between central portion 361 and the viscoelastic inserts 337 contribute to the contact-pressure reduction characteristics described herein in relation to forefoot and heel areas 323 and 325. The combination of differing materials with differing physical characteristics on either side of boundaries 350 produce a synergistic effect such that force reduction or contact pressure reduction during ambulation occurs in areas 323, 325 more readily with the combination of differing materials than would otherwise be achieved by one of the materials on its own.

In the illustrated implementations, inserts 337 and trays or chambers 335 are sized so that, whether insole 321 is unloaded or under maximum load during impact, toe-off, or other gait phases, outer edges 355 of inserts 337 do not contact opposing portions of the circumferential walls 343 of the chambers 335 in which inserts 337 have been received. As such, in both unloaded and loaded states, insole 321 has its outer edges 355 spaced from respective ones of circumferential walls 343 to define respective circumferential gaps 363 therebetween. Circumferential gaps 363 may be configured to have dimensions sufficient to maintain respective separations between the outer edges 355 of inserts 337 and respective sides 343 or walls of trays 335. Such edges may extend about the entire circumference of the viscoelastic inserts 337, but implementations where they do not extend about such entire circumference may likewise be suitable. As such, gaps 363 prevent contact between outer edges 355 of inserts 337 and walls 343 of trays 335, even when under maximum load, and thus gaps 363 allow the physical properties associated with inserts 337 (as well as stratum 333) to remain unaffected by contact between opposing portions of outer edges 355 of inserts 337 and circumferential walls or sides of trays 343 when under load during ambulation. Otherwise stated, viscoelastic inserts 337 may "flatten out" or expand in response to orthogonal force from the wearer's foot during ambulation, which, in turn, would increase the circumference defined by outer edges 355. Without gaps 363 suitably configured as disclosed herein, viscoelastic inserts 337 would impinge against polymeric material of stratum 333 at the outer edges 355 of inserts 337. Such impingement would alter compression set, rebound, and other physical characteristics of the viscoelastic material of inserts 337 during such impingement. Depending on how greatly the physical characteristics are altered by such impingement, the contact-pressure reduction properties associated with forefoot area 323 and heel area 325 may be adversely affected.

Upper and lower insert surfaces 357, 359 are spaced from each other to oppose tops and bottoms 351, 353 of trays 335 and may form an interference fit in both unloaded and loaded states, between inserts 337 and tops and bottoms 351, 353 of trays 335. In the illustrated embodiment, the trays 335 comprise apertures extending between upper and lower surfaces of middle layer 329. In such case, the overlying and underlying planar polymeric foam portions 347, 349 which bound trays 335 correspond to portions of top and bottom layers 327, 331, respectively. Alternately, middle layer 329 may have one of its upper or lower surfaces extending across the area defined by trays 335 and thereby such portion of middle layer 329 would bound either the top or bottom of trays 335 and constitute either the underlying or overlying polymeric portions 347, 349. In certain implementations, upper and lower insert surfaces 357, 359 are not adhered to tops and bottoms 351, 353 of trays 335.

Although particular dimensions may vary depending on application and shoe size, in one suitable implementation, the full range of female and male foot sizes, layers 327, 329, and 331, in their uncompressed states, have a height ranging between 6 mm and 8 mm each, with cover layer 339 ranging between 0.5 and 1.5 mm. As such, the combined heights of layers 327, 329, and 331 range from 18 mm to 24 mm. Gaps 363 between inserts 337 and walls 343 may range between 4 and 6 mm, and may be 5 mm. Linear edges 342, which comprise the innermost point of viscoelastic material, may be located so as to be anterior or inward of heel areas 325 and forefoot area 323, and quantitatively such linear edges 342 would be located between 100 mm and 102 mm from the outer edges of insole 321.

Insole 321 may be received on an outsole 365 of ambulatory protective device 221. Such outsole 365 has a bottom surface 366 configured to contact the ground when device 221 is worn and an upper surface 367. Upper surface 367 may be configured to define a concavity 369 to receive insole 321 therein.

The use of the ambulatory protective devices disclosed herein, and the functioning of insole 321 therein, is readily appreciated by the above description. The type, thickness, compression set, rebound, durometer, viscosity, and other physical characteristics of the materials used in insole 321 may be varied depending on the application, or depending on the characteristics of ambulatory protective device 321 in which insole 321 is placed. As such, insole 321 may be formed in sizes corresponding to typical sizes of shoes, and may likewise be affixed in any suitable ambulatory protective device, such as a shoe, boot, brace, walker, or cast. Insole 321 may be in the form of an insert which can be removable.

Other implementations may or may not use all of the layers described herein, and thicknesses of the layers may vary, and the shapes, perimeters, and other dimensions may likewise be varied depending on the nature of insole 321 and its associated ambulatory protective boot.

Having described the various features and structures of the implementations of this disclosure, the scope of this disclosure is not confined to the details set forth and the patent is intended to include modifications and changes which may come within and extend from the following claims.

What is claimed is:

1. An ambulatory protective device for wearing on a person's foot with a diabetic condition, the device comprising:

an insole located in the device and extending in length and width sufficient to form a footbed having forefoot and heel areas sized to receive thereon a forefoot and a heel, respectively, of a user, when the device is worn on the foot, whereby the insole has an unloaded state when not bearing weight associated with the wearer, and a maximum loaded state when bearing a preselected maximum weight to be associated with the wearer;

wherein the insole includes at least first, second, and third overlying layers, the first and third layers consisting essentially of non-viscous, resiliently compressible foam;

wherein the second layer is disposed between the first and third layers, the second layer having a stratum of non-viscous, resiliently compressible foam, the second layer having two chambers defined in the stratum by respective, inwardly facing perimeter walls, the chambers positioned at the forefoot and the heel areas of the footbed, respectively;

wherein the insole includes two, viscoelastic inserts, each of the inserts received in respective ones of the chambers, the viscoelastic inserts having respective outer perimeters and corresponding circumferences, the outer perimeters spaced about their respective circumferences from the inwardly facing perimeter walls of respective ones of the chambers to form a gap between the inserts and the inwardly facing perimeter walls;

wherein the gap has a dimensional value when the insole is in an unloaded state, the dimensional value of the gap in the unloaded state being preselected to maintain spacing between the outer perimeters of the viscoelastic inserts and the inwardly facing perimeter walls of the chambers when the insole is subjected to a predetermined, maximum weight associated with the person;

whereby, when the device is worn during ambulation, in response to a given compressive force on the forefoot area and heel area of the footbed, the corresponding insert compresses more slowly during a given unit of time than portions of the stratum adjacent the corresponding insert, and in response to lessening of a given compressive force during toe-off phase of the ambulation, the insert rebounds more quickly per the given unit of time than the portions of the stratum adjacent the corresponding insert; and whereby the heel area and the midfoot area of the footbed experience at least 30% less average maximum pressure over the given unit of time than if the footbed were without the insole.

2. The ambulatory protective device of claim 1, comprising:

a frame extending from the footbed, the frame comprising posterior and anterior portions, and configured to control ankle movement of the lower extremity, the frame having distal and proximal ends adapted to operatively engage portions of the foot and calf of the user, respectively;

an anterior ankle-foot orthosis configured to be selectively fittable to, and manually removable from, the anterior portion of the frame;

wherein the anterior ankle-foot orthosis comprises a longitudinally extending stay and at least one pair of transversely extending fingers; and wherein the at least one pair of transversely extending fingers comprise finger engagement areas; and wherein the proximal end of the frame comprises engagement portions located to oppose the finger engagement areas when the anterior ankle-foot orthosis is fitted to the frame.

3. The ambulatory protective device of claim 2, wherein the device further comprises a collar assembly configured to be selectively fittable to, and manually separable from, the proximal end of the frame.

4. The ambulatory protective device of claim 3, wherein the frame and footbed are configured to receive a lower-extremity, brace device.

5. The ambulatory protective device of claim 4, wherein the brace device is selected from the group consisting of a cast, a splint, and a bandage.

6. The ambulatory protective device of claim 5, wherein the brace device is interposed between the collar assembly and the lower extremity when worn on the lower extremity and received in the frame, and wherein the collar assembly has an engagement area oriented and configured such that when the collar assembly is fitted to the proximal end of the frame, the engagement area contacts an opposing surface of the brace device.

7. The ambulatory protective device of claim 6, wherein a distance between the distal and proximal ends of the frame define a first lever arm having a first length, wherein the frame is configured to reduce force on the foot during gait as a function of the first lever arm, and wherein the engagement area is configured to extend to locations proximal to the proximal end of the frame and to engage the brace device at said locations to define a second lever arm having a second length greater than the first length, thereby reducing force on a plantar surface of the foot when received in the ambulatory protective device.

8. The ambulatory protective device of claim 1, wherein the first layer consists essentially of ethylene vinyl acetate and the third layer consists essentially of polyurethane.

9. The ambulatory protective device of claim 8, wherein the ethylene vinyl acetate exhibits the following physical properties under associated ASTM test methods: compression set of 30%+/−10%, rebound of 46%+/−5%, split tear of 8.4 pounds per inch+/−4 pounds per inch, tensile strength of 21 psi+/−10 psi, elongation of 100-150%, density of 11 pounds per cubic foot+/−1.5 pounds per cubic foot.

10. The ambulatory protective device of claim 1, wherein the viscoelastic inserts consist essentially of a gel having a viscosity ranging between 350 to 450 centipoise.

11. The ambulatory protective device of claim 10, wherein the gel exhibits the following physical properties under associated ASTM testing methodologies: compression set of 10%+/−1%, rebound of 5%+/−1%, split tear of 11.2 lbs per inch+/−1 lb per inch, tensile strength of 14.06 psi+/−1 psi, elongation of 300%+/−10%, and density of 80 lbs per cubic foot+/−3 lbs per cubic foot.

12. The ambulatory protective device of claim 1, wherein the ambulatory protective device is selected from the group consisting of a CAM walker, a protective shoe, a protective boot, a brace, and a cast.

* * * * *